United States Patent
Szekely et al.

(10) Patent No.: US 7,605,125 B2
(45) Date of Patent: Oct. 20, 2009

(54) DNA-BINDING POLYAMIDE DRUG CONJUGATES

(75) Inventors: Zoltan Szekely, Gaithersburg, MD (US); Humcha Krishnamurthy Hariprakasha, Frederick, MD (US); Marek W. Cholody, Frederick, MD (US); Christopher Michejda, North Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 589 days.

(21) Appl. No.: 10/506,085

(22) PCT Filed: Feb. 27, 2003

(86) PCT No.: PCT/US03/06006

§ 371 (c)(1),
(2), (4) Date: Oct. 1, 2004

(87) PCT Pub. No.: WO03/072058

PCT Pub. Date: Sep. 4, 2003

(65) Prior Publication Data

US 2005/0096261 A1    May 5, 2005

Related U.S. Application Data

(60) Provisional application No. 60/361,050, filed on Feb. 27, 2002, provisional application No. 60/370,168, filed on Apr. 5, 2002.

(51) Int. Cl.
 *A61K 38/16*  (2006.01)
 *A61K 38/02*  (2006.01)
 *A61K 51/00*  (2006.01)
 *A61M 36/14*  (2006.01)
(52) U.S. Cl. .............................. 514/8; 514/2; 424/1.69
(58) Field of Classification Search ............... 514/2
   See application file for complete search history.

(56) References Cited

U.S. PATENT DOCUMENTS 4,874,863 A    10/1989  Brana et al.
6,060,608 A     5/2000  Boger

OTHER PUBLICATIONS

Boger et al., *J. Org. Chem.*, 61, 4894-4912 (1996).
Chang et al., *J. Am. Chem. Soc.*, 122, 4856-4864 (2000).
Dervan, *Bioorganic and Medicinal Chemistry*, 9, 2215-2235 (2001).
Dickinson et al., *Proc. Natl. Acad. Sci. U.S.A.*, 95, 12890-12895 (1998).
Gottesfeld et al., *Nature*, 387, 202-205 (1997).
Gupta et al., *Anti-Cancer Drug Design*, 11, 581-596 (1996).
Jia et al., *Chem. Commun.*, 119-120 (1999).
Jia et al., *Heterocyclic Communications*, 4(6), 557-560 (1998).
Jia et al., *Synlett*, 5, 603-606 (2000).
Maeshima et al., *Embo Journal*, 20(12), 3218-3228 (2001).
Reddy et al., *Current Medicinal Chemistry*, 8, 475-508 (2001).
Soto et al., *Nucleic Acids Research*, 29(17), 3638-3645 (2001).
Wang et al., *Gene*, 149, 63-67 (1994).
Wurtz et al., *Org. Lett.*, 3(8), 1201-1203 (2001).

*Primary Examiner*—Andrew D. Kosar
*Assistant Examiner*—Maury Audet
(74) *Attorney, Agent, or Firm*—Leydig, Voit & Mayer, Ltd.

(57) ABSTRACT

A conjugate of formula: $V—(Y)_a—Z-T$: (I), $T-X—B—(Y)_a—Z-T'$: (II), $V—(Y)_a\ Z—(Y')_a\ V'$: (III), $T-X—B—(Y)_a—Z—(Y')_a—X'—B'-T'$: (IV), $V—(Y)_a—Z—(Y')_a—X—B-T$: (V), $V—(Y)_a—Z—X—B—Z'—(Y')_a—(V')_b$: (VI), or $(W)_a—(Y)_b—[(Z)_c—(Y')_d—(X—B)_e—(Y'')_f—(Z')_g]_h—(Y\ldots)_i—(W')_j$: (VII), in which W and W' are independently a DNA intercalator or terminal subunit, V and V' are independently a DNA intercalator, X and X' are independently a DNA alkylator, B and B' are the same or different and each is a heteroaromatic residue that is attached to the Nterminus of an alkylator subunit (X or X'), Y, Y', Y'' and Y''' are independently a linker, T and T' are independently terminal subunits, Z and Z' are independently a polyamide group that binds to the minor groove of DNA, a, b, c, d, f, g, i, and j are independently 0 to 5, and e and h are independently 1 to 5, a composition comprising a conjugate of any of formulae (I)-(VII) and a carrier, and a method for treating cancer in a mammal comprising administering an effective amount of a conjugate of any of formulae (I)-(VII) or a composition comprising same.

32 Claims, 6 Drawing Sheets

DNA-BINDING POLYAMIDE DRUG CONJUGATES

CROSS-REFERENCE TO RELATED PATENT APPLICATIONS

This application is the U.S. national phase of International Patent Application No. PCT/US03/06006, which was filed on Feb. 27, 2003, and which claims the benefit of both U.S. Provisional Patent Application No. 60/361,050, which was filed on Feb. 27, 2002, and U.S. Provisional Patent Application No. 60/370,168, which was filed on Apr. 5, 2002.

TECHNICAL FIELD OF THE INVENTION

The present invention relates to conjugates comprising one or more DNA intercalator(s) and/or one or more DNA alkylator(s) linked to one or more polyamide DNA minor groove binder(s). The conjugates of the present invention and compositions thereof are useful in the treatment of cancer in a mammal.

BACKGROUND OF THE INVENTION

Specificity is one of the goals of modern drug design. It is known that DNA is a target of most antitumor drugs, since many antitumor drugs are effective by inhibiting nucleic acid (DNA or RNA) or protein synthesis. There are many potent antitumor compounds with a wide spectrum of activities against many tumor cell lines, both in vitro and in vivo, but because these compounds are so toxic, normal cells and tissue can be adversely affected as well. Many researchers have proposed ideas of increasing selectivity, while maintaining a high degree of toxicity.

Polyamides that contain polypyrrole carboxamide and/or polyimidazole carboxamide subunits are known to bind specifically to the minor groove of DNA (see, for example, Dervan, *Bioorganic and Medicinal Chemistry*, 9: 2215-2235 (2001); Soto et al., *Nucleic Acids Research*, 29(17): 3638-3645 (2001); and Reddy et al., *Current Medicinal Chemistry*, 8: 475-508 (2001)). Such polyamides can be designed so that they bind to DNA in a sequence-specific manner. These polyamide minor groove binders can inhibit or suppress gene functions. The polyamide minor groove binders bis-lexitropsins (Reddy et al., *Current Medicinal Chemistry*, 8: 475-508 (2001)), for example, have shown enhanced cytotoxic activity against KB human nasopharyngeal carcinoma. It also has been shown that double-stranded hairpin polyamides can permeate cellular and nuclear membranes of eukaryotes and, when targeted to promoter regions, can inhibit specific gene expression (Gottesfeld et al., *Nature*, 387: 202-205 (1997); and Dickinson et al., *Proc. Natl. Acad. Sci. U.S.A.*, 95: 12890-12895 (1998)). In addition to the double-stranded hairpin polyamides, the single-stranded analogues have been proven to carry out inhibition of gene expression in Drosophila (Maeshima et al., *The EMBO Journal*, 20: 3218-3228 (2001)).

Researchers have linked toxic compounds to polyamide sequences, such as netropsin, distanycin and lexitropsin (see, for example, Chang et al., *J. Am. Chem. Soc.*, 122: 4856-4864 (2000); Gupta et al., *Anti-Cancer Drug Design*, 11(8): 581-596 (1996); Jia et al., *Heterocyclic Commun.*, 4(6): 557-560 (1998); Jia et al., *Chem. Commun*, (2): 119-120 (1999); Jia et al., *Synlett*, (5): 603-606 (2000); and Wang et al., *Gene*, 149 (I): 63-67 (1994)). While these conjugates may show some antitumor activity, the conjugates, themselves, have the wrong geometric and/or electronic parameters that hinder the fit in the minor groove. A poor fit can result in a lower efficacy or selectivity as well as higher side effects due to nonspecific binding to untargeted genomic elements or DNA sequences.

Thus, there still exists a need for therapeutic conjugates that have improved antitumor selectivity and DNA sequence-specific binding properties. Ideally, these conjugates would elicit fewer side effects and less damage to healthy cells and tissue. Effective therapeutic conjugates can be designed rationally, because an understanding of the geometry of the conjugates enables a better fit of the drug into the shape of the minor groove pocket, thereby increasing the sequence-specificity. The present invention provides such therapeutic conjugates. The conjugates of the present invention bind in the minor groove of DNA in a sequence-specific manner and effectively deliver a toxic moiety.

BRIEF SUMMARY OF THE INVENTION

The present invention provides a conjugate of formula:

in which V is a DNA intercalator, X is a DNA alkylator, B is a heteroaromatic residue that is attached to the N-terminus of the alkylator subunit (X), Y is a linker, T and T' are the same or different and each is a terminal subunit, Z is a polyamide group that binds to the minor groove of DNA, and a is 0 or 1, provided that when V is naphthalimide, then Z is not lexitropsin, and further provided that when V is doxorubicin, then Z is not netropsin or distatnycin. In addition, the present invention provides a conjugate of formula:

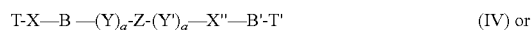

in which V and V' are the same or different and each is a DNA intercalator, X and X' are the same or different and each is a DNA alkylator, B and B' are the same or diffent and each is a heteroaromatic residue that is attached to the N-terminus of an alkylator subunit (X or X'), Y and Y' are the same or different and each is a linker, T and T' are the same or different and each is a terminal subunit, Z is a polyamide group that binds to the minor groove of DNA, and a is 0 or 1. The present invention further provides a conjugate of formula:

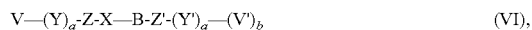

in which V and V' are the same or different and each is a DNA intercalator, X is a DNA alkylator, B is a heteroaromatic residue that is attached to the N-terminus of the alkylator subunit (X), Y and Y' are the same or different and each is a linker, Z and Z' are the same or different and each is a polyamide group that binds to the minor groove of DNA, and a and b are independently 0 or 1.

In addition, the present invention provides a hybrid conjugate of formula:

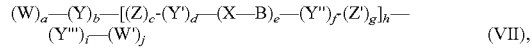

in which W and W' are the same or different and each is a DNA intercalator (V or V') or terminal subunit (T or T'), X is a DNA alkylator, B is a heteroaromatic residue that is attached to the N-terminus of the alkylator subunit (X), Y, Y', Y" and Y'" are the same or different and each is a linker, Z and Z' are the same or different and each is a polyamide group that binds to the minor groove of DNA, a is 0-5, b is 0-5, c is 0-5, d is 0-5, e is 1-5, f is 0-5, g is 0-5, h is 1-5, i is 0-5, and j is 0-5.

Further provided by the present invention is a composition comprising a conjugate of any of formulae (I)-(VI) and a carrier.

Still further provided by the present invention is a method for treating cancer in a mammal comprising administering to a mammal in need thereof an effective amount of a conjugate of any of formulae (I)-(VI) or a composition thereof.

DETAILED DESCRIPTION OF THE INVENTION

Figure 1:
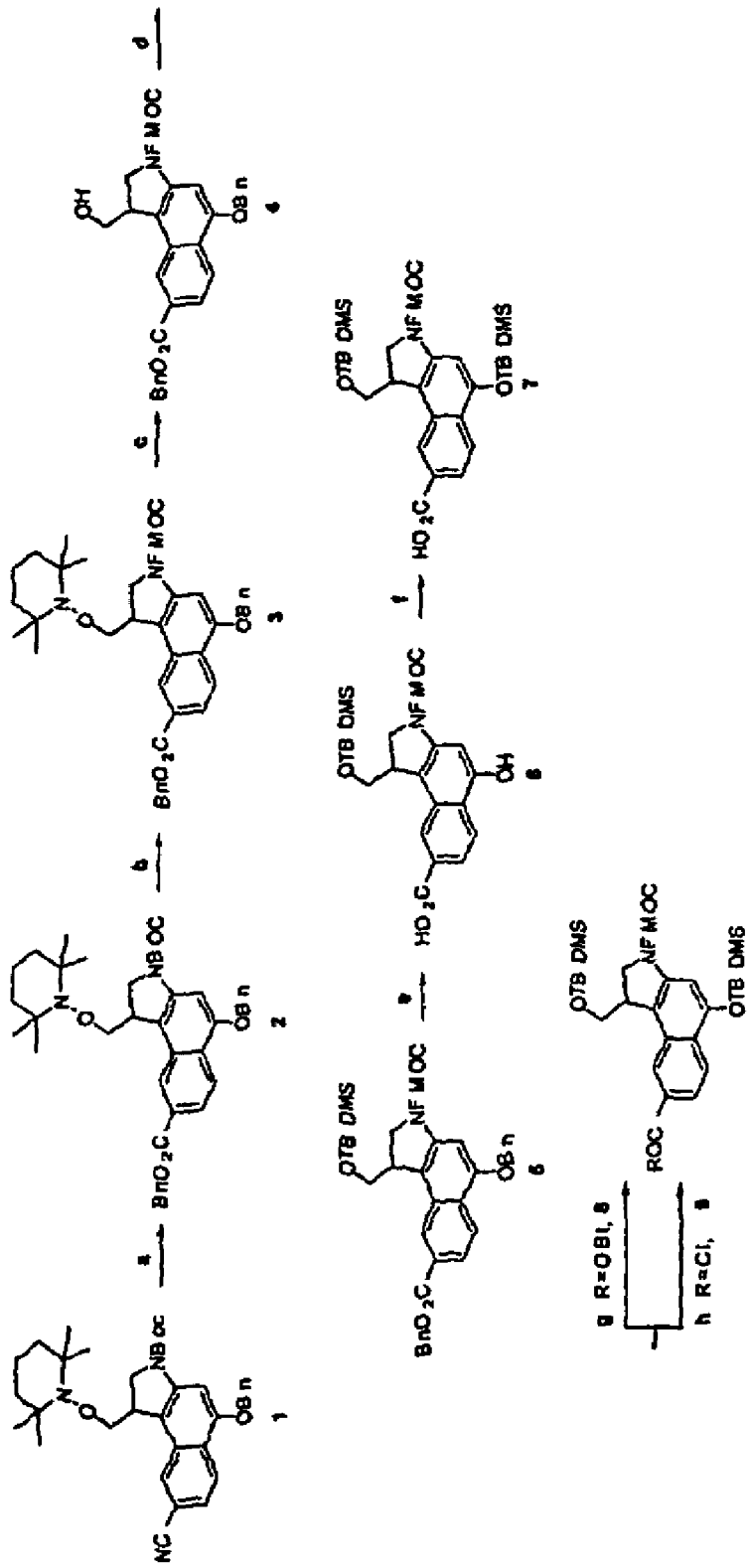
FIG. 1 depicts the synthetic scheme of {1-(chloromethyl)-5-hydroxy-1,2-dihydro-3H-benz[e]indole-8-carboxylic acid} ("CBIr"), a rigid DNA alkylator.

The present invention provides conjugates that comprise one or more polyamide minor groove binder(s) linked to one or more DNA intercalator(s) and/or DNA alkylator(s). The conjugates bind specifically to preselected genes, i.e., coding sequence or control sequence, such as promoter or enhancer, effectively inhibiting the genes' functions. Therefore, the conjugates are useful as therapeutic agents in the treatment of cancer, in which a known gene is responsible for the survival of the cancer cell.

In one aspect, the invention provides a conjugate of formula (I) or (II):

   (I) or

   (II), in which V is a DNA intercalator, X is a DNA alkylator, B is a heteroaromatic residue that is attached to the N-terminus of the alkylator subunit (X), Y is a linker, T and T' are the same or different terminal subunits, Z is a polyamide group that binds to the minor groove of DNA, and a is 0 or 1, provided that when V is naphthalimide, then Z is not lexitropsin, and further provided that when V is doxorubicin, then Z is not netropsin or distamycin.

In another aspect, the present invention provides a conjugate of formula:

   (I),

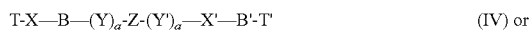   (IV) or

   (V), in which V and V' are the same or different and each is a DNA intercalator, X and X' are the same or different and each is a DNA alkylator, B and B' are the same or diffent and each is a heteroaromatic residue that is attached to the N-terminus of an alkylator subunit (X or X'), Y and Y' are the same or different and each is a linker, T and T' are the same or different and each is a terminal subunit, Z is a polyamide group that binds to the minor groove of DNA, and a is 0 or 1.

In yet another aspect, the present invention provides a conjugate of formula:

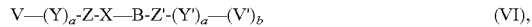   (VI), in which V and V' are the same or different and each is a DNA intercalator, X is a DNA alkylator, B is a heteroaromatic residue that is attached to the N-terminus of the alkylator subunit (X), Y and Y' are the same or different and each is a linker, Z and Z' are the same or different and each is a polyamide group that binds to the minor groove of DNA, and a and b are independently 0 or 1.

In addition, the present invention provides a hybrid conjugate of formula:

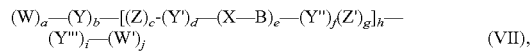   (VII), in which W and W' are the same or different and each is a DNA intercalator (V or V') or terminal subunit (T or T'), B is a heteroaromatic residue that is attached to the N-terminus of the alkylator subunit (X), Y, Y', Y" and Y'" are the same or different and each is a linker, Z and Z' are the same or different and each is a polyamide group that binds to the minor groove of DNA, X is a DNA alkylator, a is 0-5, b is 0-5, c is 0-5, d is 0-5, e is 1-5, f is 0-5, g is 0-5, h is 1-5, i is 0-5, and j is 0-5. Preferably, a, b, c, d, f, g, i, and j are independently 0-4, more preferably 0-3, even more preferably 0-2, and most preferably 0 or 1. Preferably, e and j are independently 1-5, more preferably 1-4, even more preferably 1-3, and most preferably 1 or 2. When h is 2 or higher, compounds of formula (VII) preferably comprise 2 or more polyamide groups (Z, Z') that are the same or different and 2 or more alkylators (X, X') that are the same or different.

The DNA intercalator (V and/or V') is any suitable moiety that can intercalate between selected base pairs of DNA, preferably in the minor groove, and is toxic to the cancer cells to which it binds. Alternatively, the DNA intercalator can form covalent bonds with nucleophilic positions on the DNA bases. Specific examples of DNA intercalators include, but are not limited to, substituted or unsubstituted anthracyclines, such as doxorubicin or daunorubicin; substituted or unsubstituted imidazoacridone; substituted or unsubstituted 3-nitrophthalamide; and substituted or unsubstituted 3-aminophthalamide. Any suitable moieties can be used to substitute the aforementioned intercalators, provided that the moieties do not adversely affect the ability of the intercalator to intercalate between selected base pairs of DNA or to form covalent bonds with nucleophilic positions on DNA bases. For example, acceptable substituents include, but are not limited to, hydroxy, $C_{1-12}$ alkoxy, acyloxy, halo or benzyl, acetyl, carboxyl, carboxy-$C_{1-12}$ alkyl, such as carboxymethyl, carboxyethyl, carboxy-$C_{1-12}$ alkylamido, carboxy-$C_{1-12}$ dialkylamido, carboxamido, amino, $C_{1-12}$ alkylamino, $C_{1-12}$ dialkylamino, $C_{1-12}$ alkylcarbonyl, $C_{6-30}$ arylamino, $C_{6-30}$ diarylamino, cyano, tolyl, xylyl, mesityl, anisyl, pyrrolidinyl, formyl, dioxane, thio, $C_{1-12}$ alkylthio, $C_{6-30}$ aryl, $C_{5-30}$ heteroaryl, such as pyranyl, pyrrolyl, furanyl, thiophenyl, thiazolyl, pyrazolyl, pyridinyl, or pyrimidinyl, phenoxy, benzyloxy, phenylcarbonyl, benzylcarbonyl, nitrophenyl $C_{1-12}$ trialkylsilyl, nitro, sulfonyl, nitrobenzyl, $C_{1-12}$ trialkylammonium, $C_{1-12}$ alkyl, $C_{3-8}$ cycloalkyl, tetrahydrofuranyl, tetrahydropyranyl, piperidinyl and morpholinyl.

The DNA alkylator (X and/or X') is any suitable sequence-selective alkylating agent that is toxic to DNA for which it is selective. Preferably, the DNA alkylator is a rigid alkylator or a flexible alkylator. In particular, the rigid alkylator is preferably {1-(chloromethyl)-5-hydroxy-1,2-dihydro-3H-benz[e]indole-8-carboxylic acid} ("CBIr"):

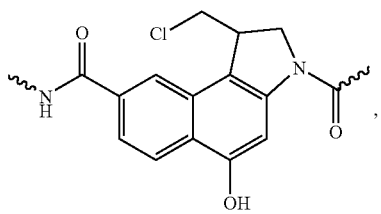

that is optionally further substituted, and the flexible alkylator is 2-{1-(chloromethyl)-5-hydroxy-1,2-dihydro-3H-benz[e]indol-8-yl}acetic acid ("CBIf"):

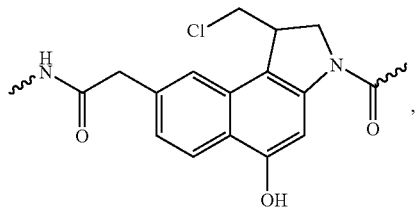

that is optionally further substituted, or 8-(aminomethyl)-1-(chloromethyl)-5-hydroxy-1,2-dihydro-3H-benz[e]indole ("CBIa"):

that is optionally further substituted. These compounds are part of a class of compounds based on a cyclopropanobenzindole (CBI) skeleton that is known to be extremely cytotoxic (e.g., $IC_{50}$ in the nano- to picomolar range). With respect to CBI analogs, preferably the linking moiety or polyamide groove binder is connected at the C3 and C7 positions, as shown in the following structure:

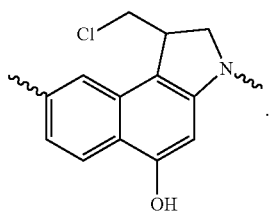

Conjugates in which the connectivity of the CBI analog is through the C3 and C8 positions are generally not preferred because the geometry of the conjugate is not ideal for fitting in the minor groove of DNA. The CBI analogs described above comprise an amino acid or amino alkyl moiety, thereby allowing them to be part of the polyamide minor groove binder sequence. Therefore, conjugates that comprise such amino acid or amino alkyl DNA alkylators do not necessarily require an additional linker to link the alkylator to the polyamide minor groove binder.

It is understood for purposes of this invention that the CBI moiety can be in an "open" form or a "closed" form as follows:

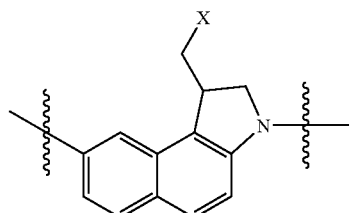
"open" or "seco" forma

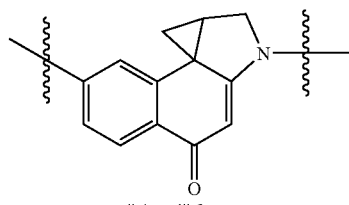
"closed" form x=halide, esters such as but not limited to mesylate, tosylate, nitroureas, nitrocarbamates. Their capacity to alkylate DNA is virtually equivalent.

The alkylator subunits have been designed so that they can be incorporated into various positions of the DNA sequence-recognizing minor groove binders. In other words, the CBI derivatives function as constituent units of the minor groove binding structure. This is unlike the CBI derivatives designed earlier, which can be attached to the C-terminal or N-terminal end of the polyamide chains but not within the chain. The difference between the present inventive CBI derivatives and the other constituent units of the DNA-recognizing sequences is that they react covalently with the DNA in a highly sequence-specific manner imparted by their particular placement within the sequence. Besides the increased specificity of binding, the embedded CBI units can decrease the chances of unspecific alkylation of DNA, which is more likely when CBI-terminated binders (at either ends) interact with DNA.

The polyamide group that binds to the minor groove of DNA (Z and/or Z') is any suitable polyamide sequence that recognizes specific DNA sequences through minor groove binding. Preferably, the polyamide sequence comprises one or more substituted or unsubstituted polypyrrole carboxamide, one or more substituted or unsubstituted polyimidazole carboxamide, or combinations thereof. More preferably, the polyamide minor groove binder comprises subunits of 4-amino-1-methylpyrrole-2-carboxylic acid, 4-amino-1-methylimidazole-2-carboxylic acid, 4-amino-1-methyl-3-hydroxypyrrole-2-carboxylic acid, γ-amino-butyric acid, α,γ-diamino-butyric acid, glutamic acid, 8-amino-3,6-dioxanioic acid, β-alanine, 4-amino-benzoic acid, 3-amino-benzoic acid, 2-aminothiazole-5-carboxylic acid, 4-aminothiophene-2-carboxylic acid, 5-aminobenzthiophene-2-carboxylic acid, 5-aminobenzoxazole-2-carboxylic acid, 5-aminobenzimidazole-2-carboxylic acid or combinations thereof. It is understood that the longer the polyamide sequence, the more DNA-selective it is considered to be. The polyamide minor groove binder preferably contains 20 or fewer amide subunits, more preferably 10 or fewer amide subunits, more preferably 8 or fewer amide subunits, more preferably 6 or fewer amide subunits, and most preferably 5 or fewer amide subunits. A preferred conjugate will contain one or more polyamide minor groove binder(s) made up of 4 or 5 amide subunits.

The heteroaromatic residue (B) that is attached to the N-terminus of the alkylator subunit (X or X') increases the activity of the alkylator, resulting in an agent with much higher cytotoxicity. Preferably, any unit listed for Z (minor groove binder) is suitable for the B subunit. More preferably, bicyclic or tricyclic molecules, such as indoles, benzofuranes and the like, should be used.

Conjugates of the present invention can comprise one polyamide minor groove binder (i.e., single-stranded) or more than one polyamide minor groove binder (e.g., double-stranded). In the case of double-stranded conjugates, the conjugate can optionally form a hairpin structure. Without wishing to be bound to any particular theory, it is believed that an entire hairpin structure can fit into the minor groove and has much stronger binding than its corresponding single-stranded conjugate.

The linker comprises any moiety that can form a chemical bond between the polyamide minor groove binder (i.e., Z and/or Z') and the intercalator (V and/or V') or the DNA alkylator (X and/or X'). The linker can optionally bind to the minor groove of DNA but can have little to no ability for sequence-specific interaction. The linker can be of any suitable charge, length and/or rigidity, but preferably the linker is bifunctional and/or comprises one or more amino groups. At physiological pH, the amino group is protonated and can also bind to DNA. The amino group can be primary, secondary or tertiary. Preferably, the amino group comprises a moiety selected from the group consisting of amino, $C_1$-$C_{12}$ alkylamino, $C_1$-$C_{12}$ dialkylamino, cycloalkylamino, piperazinyl, piperidinyl, pyrazinyl, purinyl, pyridazinyl, pyrrolidinyl, oxazolyl, isooxazolyl, quinolinyl, isoquinolinyl, byrimidinyl, morpholinyl, thiazolyl, isothiazolyl, quinoxalinyl, quinazolinyl, pyrrolyl, imidazolyl and an amino acid residue. Specific examples of suitable linkers include, but are not limited to, N,N'-bis(aminopropyl)piperazine, N,N'-bis(aminopropyl) methylamine, 8-amino-3,6-dioxaoctanoic acid, spermidine and β-alanine.

The conjugate can be optionally terminated at either end with a moiety that forms a chemical bond with either the N-terminus or the C-terminus of the conjugate. The terminal subunit (T and/or T') can comprise any suitable functional group, but preferably contains at least one amino group, amidine, guanidine or a carboxamide moiety. At physiological pH, the amino group is protonated and can also bind to the DNA sequence. Typical terminal subunits include, but are not limited to, N,N-dimethylglycine, guanidino acetic acid, 3-aminopropylamidine, glycinol, N,N-dimethylaminopropylamine, N-formyl, N-acetyl, N-propionyl and N-benzoyl.

The conjugate of any of formulae (I)-(VII) binds to DNA, preferably in the minor groove. The conjugate is sequence-selective and binds to at least 5 base pairs in DNA, preferably at least 7 base pairs in DNA, more preferably at least 9 base pairs in DNA, and most preferably at least 10 base pairs in DNA. Depending on the specific polyamide minor groove binder and intercalator and/or alkylator selected for the conjugate, the conjugate can bind to a G-C rich DNA sequence or to an A-T rich DNA sequence. Those skilled in the art will understand how to make such selections for each element of the conjugate in order to bind to a G-C or A-T rich DNA sequence. For example, DNA alkylators such as CBI analogs, as described herein, bind covalently to adenine residues through the minor groove. Therefore, conjugates comprising a CBI analog can be used to bind selectively to A-T rich DNA sequences. Alternatively, conjugates that comprise a phthalimide or anthracycline residue tend to favor G-C rich DNA sequences. The selection of subunits of the polyamide minor groove binder allows for the preparation of sequences that can preferentially bind to G-C or A-T rich DNA sequences. For example, N-methylimidazole preferably will bind to guanosine, whereas N-methylpyrrole preferably will bind to cytosine, adenine, and thymidine.

A preferred conjugate of formula (I) is:

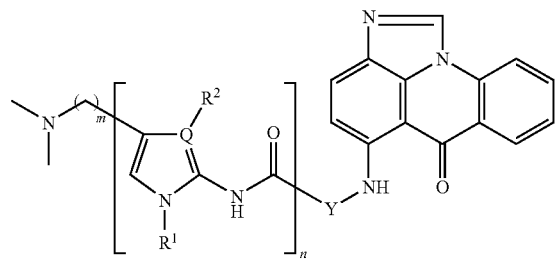

in which Y is a linker; in each repeat unit, Q is independently N or CH; $R^1$ and $R^2$ are selected from the group consisting of hydrogen, $C_1$-$C_{12}$ alkyl, hydroxy, and halo; and n and m are independently 1 to 6. Another preferred conjugate of formula (I) is:

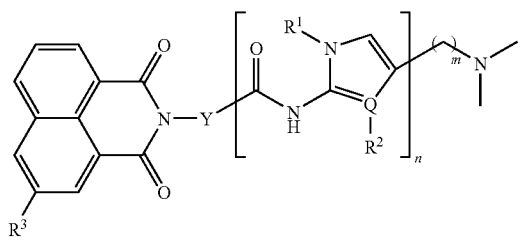
in which $R^3$ is —$NO_2$ or —$NH_2$, Y is a linker; in each repeat unit, Q is independently N or CH; $R^1$ and $R^2$ are selected from the group consisting of hydrogen, $C_1$-$C_{12}$ alkyl, hydroxy, and halo; and n and m are independently 1 to 6. An especially preferred example of a conjugate of formula (I) is:
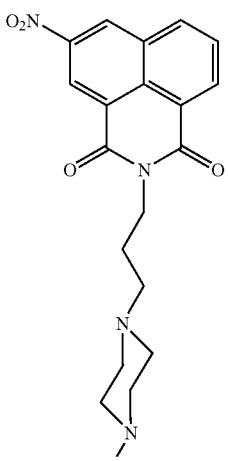
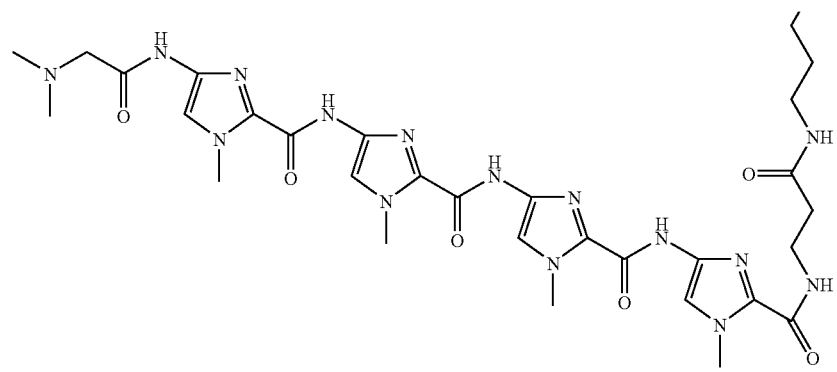

Another preferred conjugate of formula (I) is:
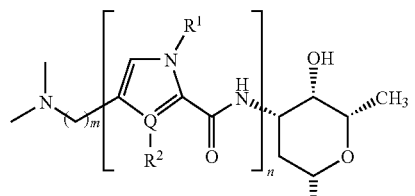
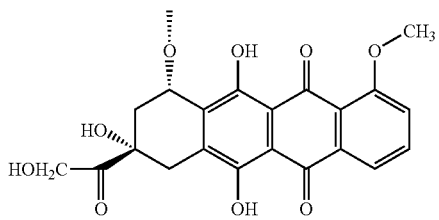
in which in each repeat unit, Q is independently N or CH; $R^1$ and $R^2$ are selected from the group consisting of hydrogen, $C_1$-$C_{12}$ alkyl, hydroxy, and halo; and n and m are independently 1 to 6, provided that when Q in each repeat unit is CH, $R^1$ is $CH_3$ and $R^2$ is H, then n is not 1-3. An especially preferred conjugate of formula (I) is:
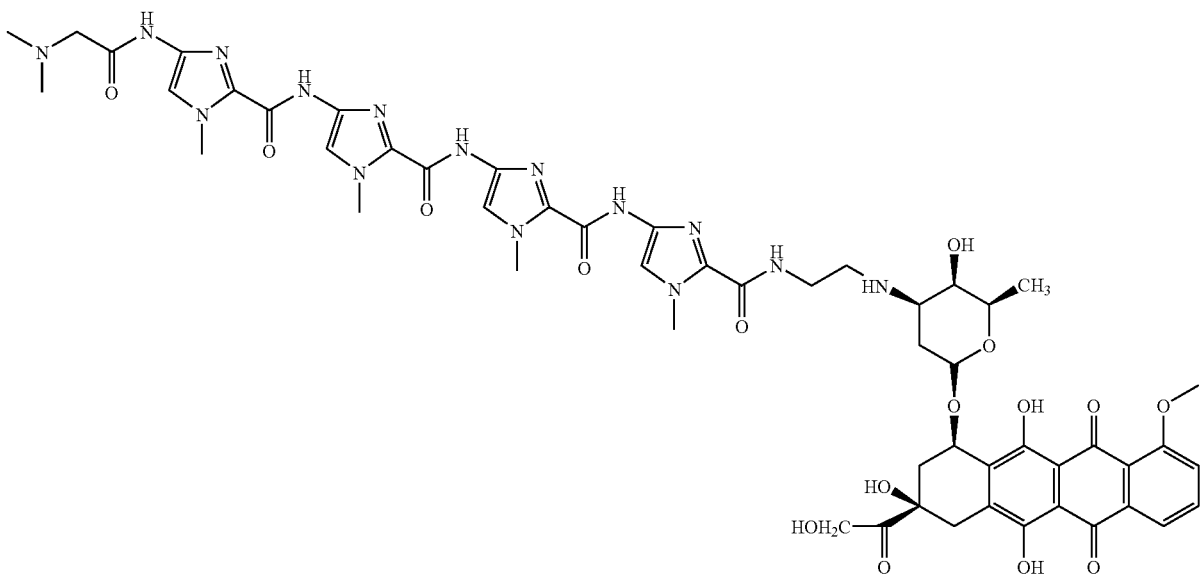

A preferred conjugate of formula (II) is:

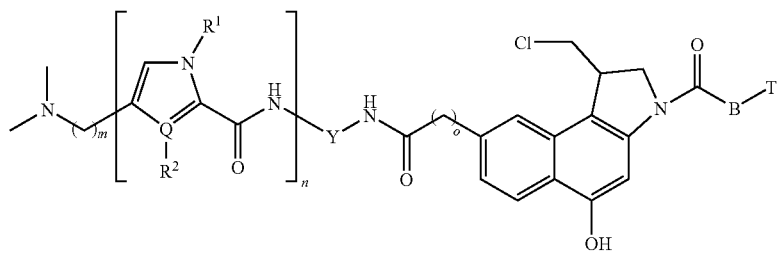

in which Y is a linker; in each repeat unit, Q is independently N or CH; B is a heteroaromatic residue as defined above; T is a terminal subunit as defined above; $R^1$ and $R^2$ are selected from the group consisting of hydrogen, $C_1$-$C_{12}$ alkyl, hydroxy, and halo; n and m are independently 1 to 6; and 0 is 0 or 1. An especially preferred example of a conjugate of formula (II) is:

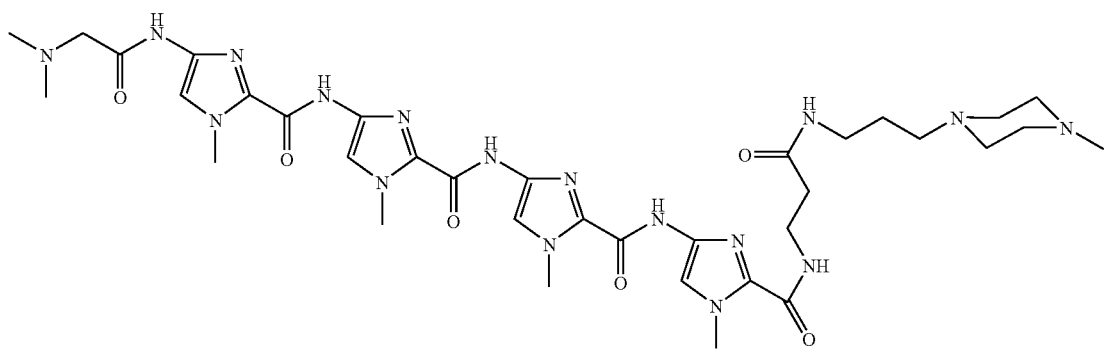

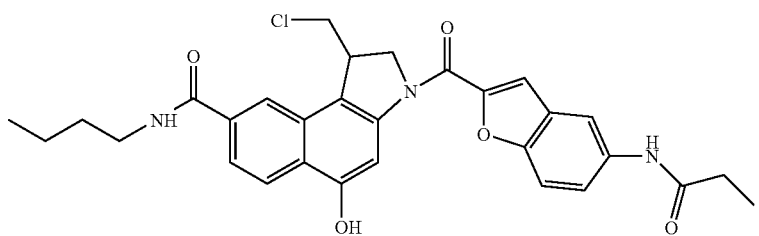

Another preferred conjugate of formula (II) is:

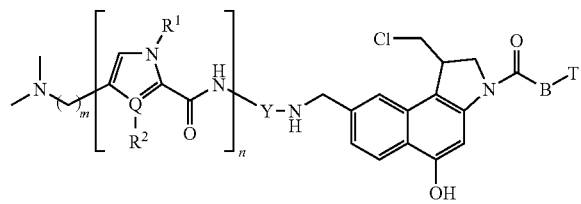

in which Y is a linker; in each repeat unit, Q is independently N or CH; B is a heteroaromatic residue as defined above; T is a terminal subunit as defined above; $R^1$ and $R^2$ are selected from the group consisting of hydrogen, $C_1$-$C_{12}$ alkyl, hydroxy, and halo; and n and m are independently 1 to 6.

A preferred conjugate of conjugate of formula (III) is:

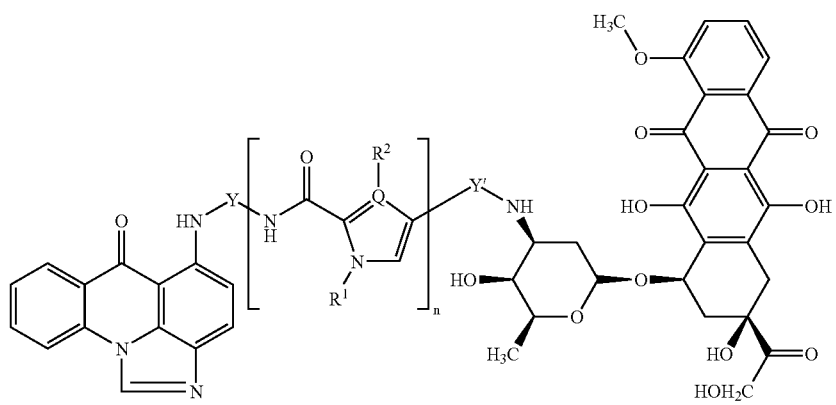

in which Y and Y' can be the same or different and each is a linker; in each repeat unit, Q is independently N or CH; $R^1$ and $R^2$ are selected from the group consisting of hydrogen, $C_1$-$C_{12}$ alkyl, hydroxy, and halo; and n is 1 to 6. An especially preferred conjugate of formula (II) is:

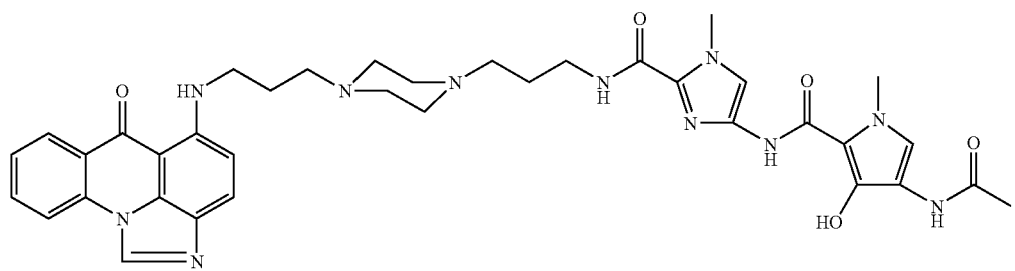

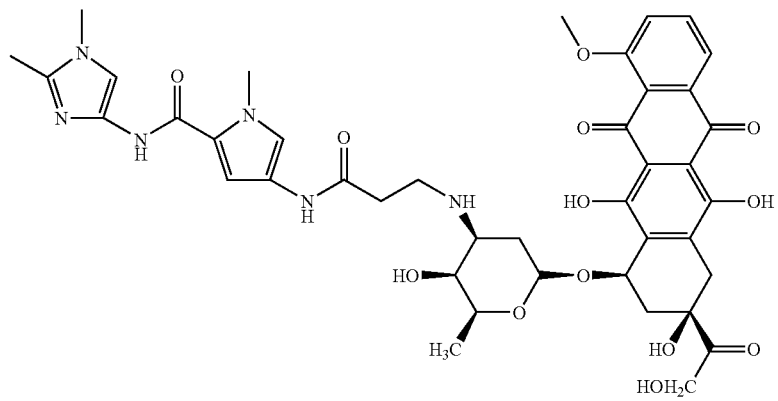

A preferred conjugate of formula (IV) is:

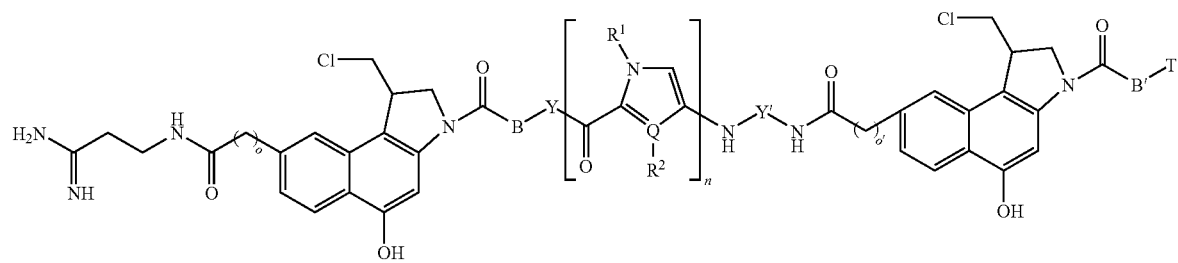

15 in which Y and Y' can be the same or different and each is a linker; in each repeat unit, Q is independently N or CH; B and B' are the same or different and each is a heteroaromatic residue as defined above; T is a terminal subunit as defined above; $R^1$ and $R^2$ are selected from the group consisting of hydrogen, $C_1$-$C_{12}$ alkyl, hydroxy, and halo; n is 1 to 6; and o and o' are independently 0 or 1. An especially preferred conjugate of formula (IV) is:

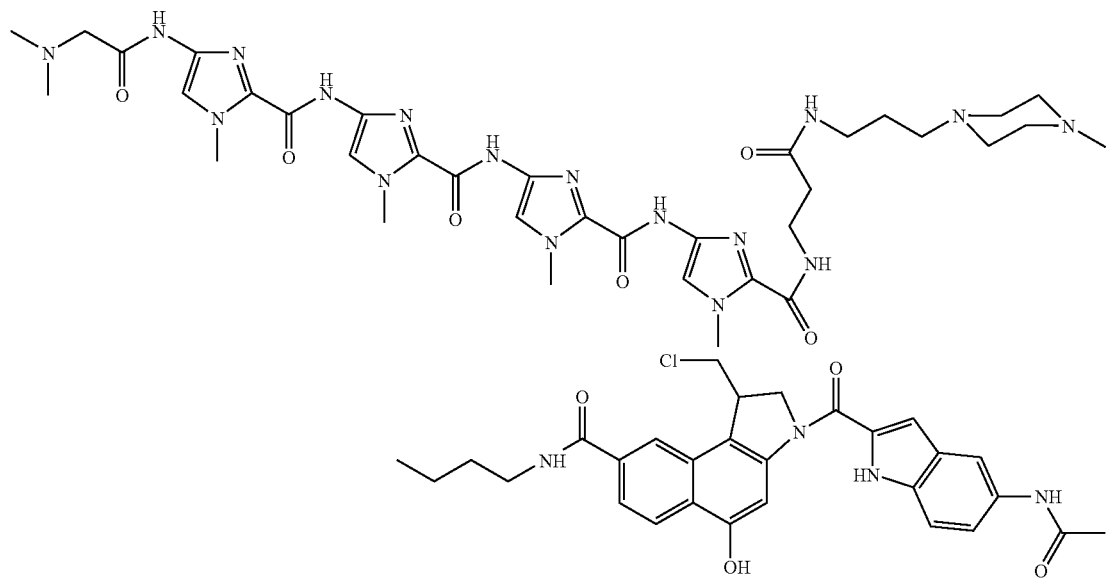

A preferred conjugate of formula (V) is:

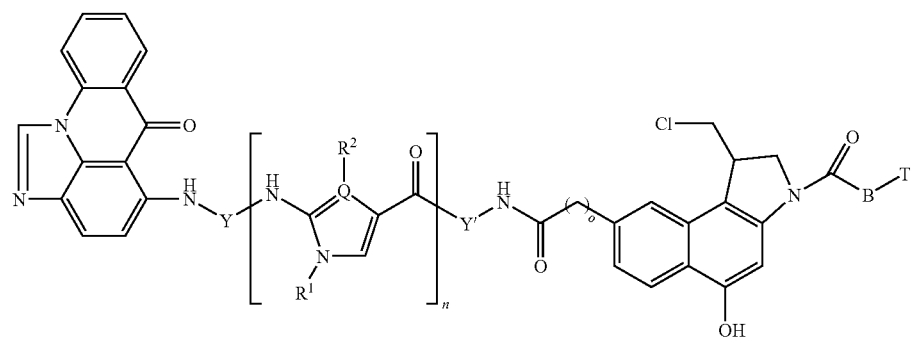

in which B is a heteroaromatic residue as defined above; T is a terminal subunit as defined above; Y and Y' can be the same or different and each is a linker, in each repeat unit, Q is independently N or CH; $R^1$ and $R^2$ are selected from the group consisting of hydrogen, $C_1$-$C_{12}$ alkyl, hydroxy, and halo; n is 1 to 6; and o is 0 or 1. An especially preferred conjugate of formula (V) is:

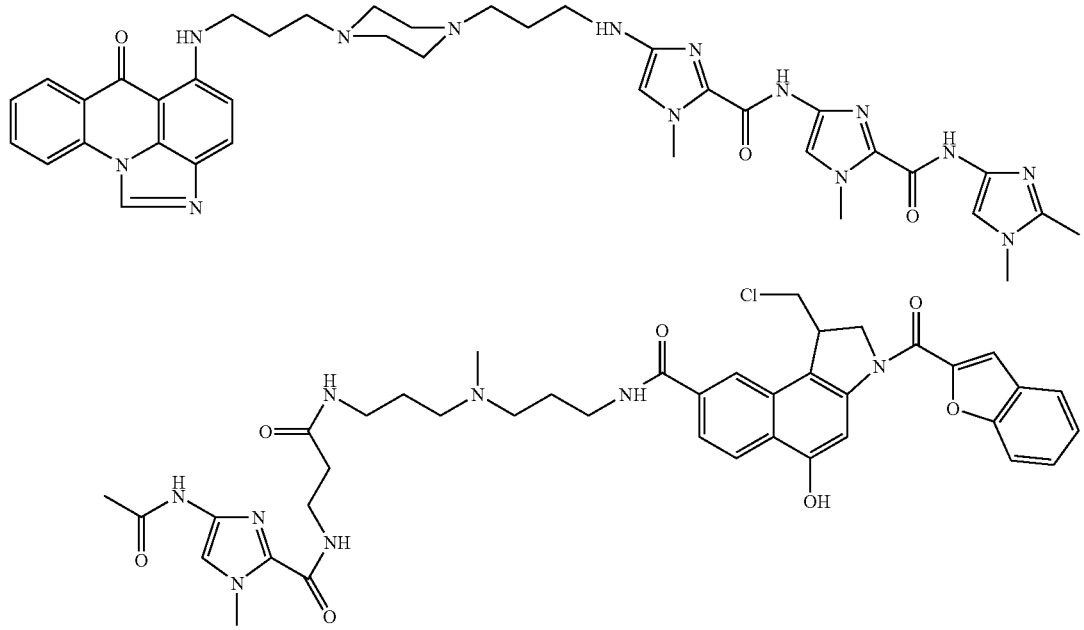

A preferred conjugate of formula (VI) is:

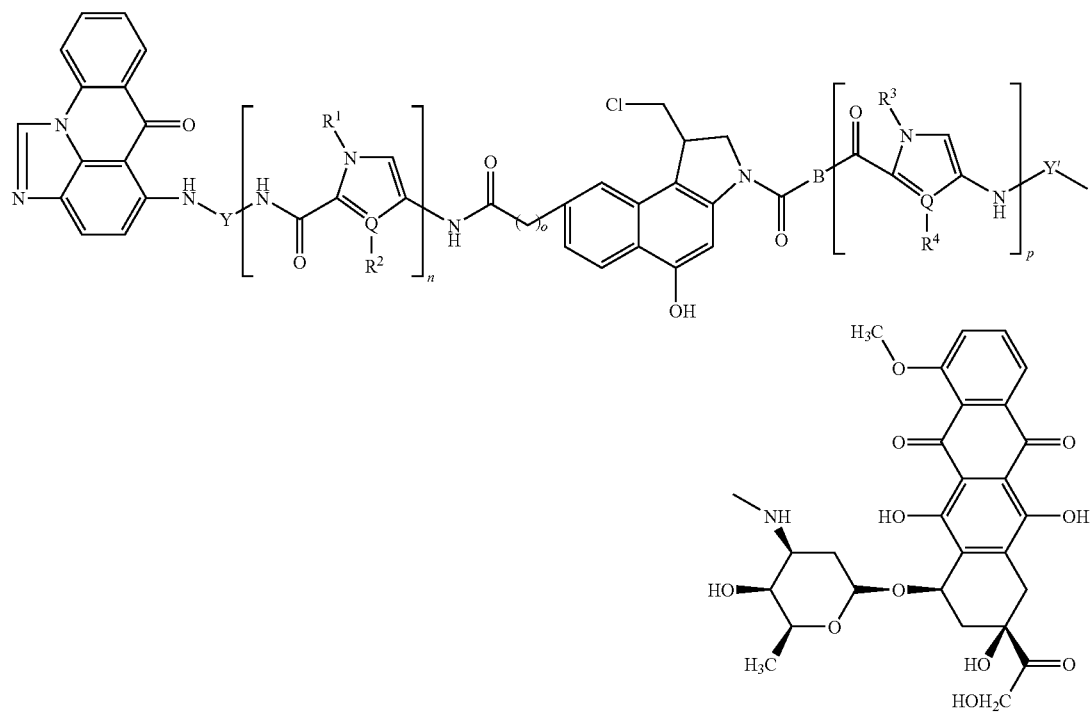

in which Y and Y' can be the same or different and each is a linker; B is a heteroaromatic residue as defined above; in each repeat unit, Q is independently N or CH; $R^{14}$ are selected from the group consisting of hydrogen, $C_1$-$C_{12}$ alkyl, hydroxy, and halo; n and p independently are 1 to 6; and o is 0 or 1. An especially preferred conjugate of formula (VI) is:
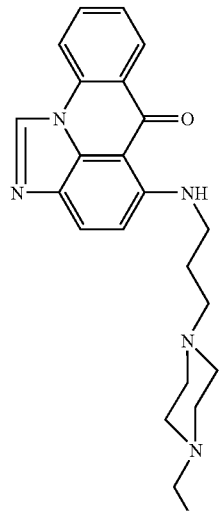
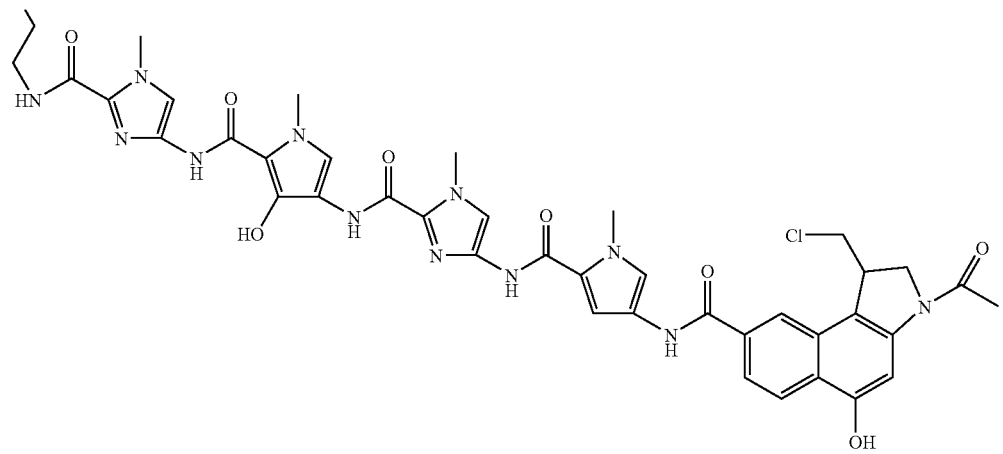
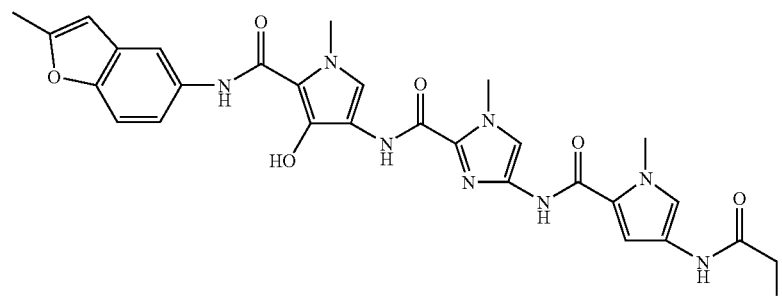

-continued
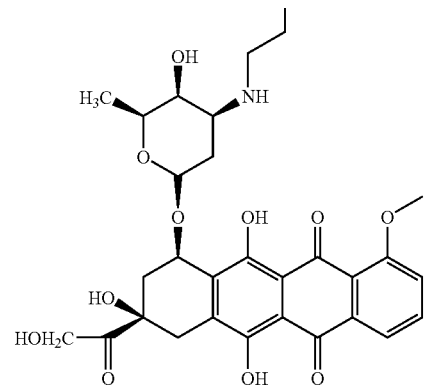
Another especially preferred conjugate of formula (VI) is:
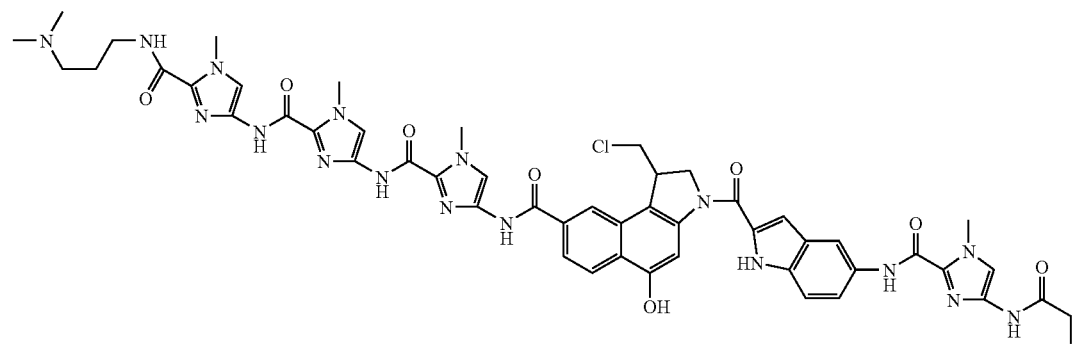
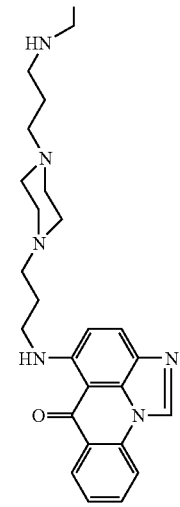

A preferred conjugate of formula (VI), (in which a=b=e=hj=1 and c=d=f=g=i=0) is:
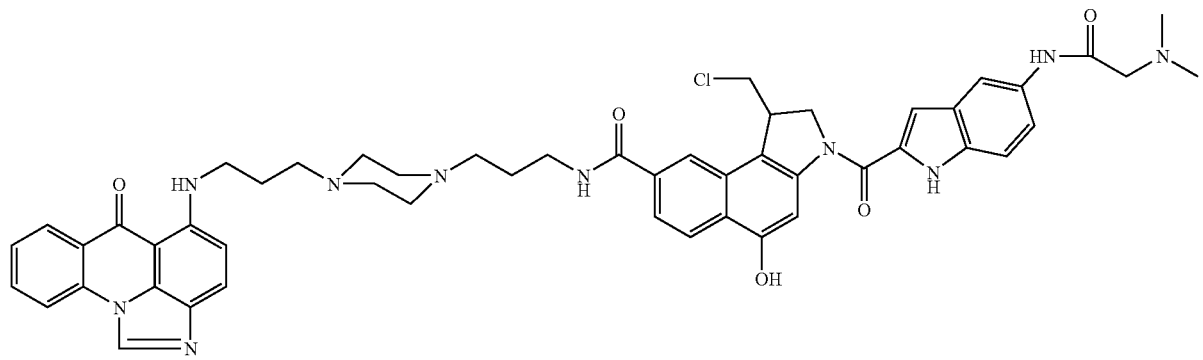
The imidazoacridine moriety can be substituted in position 8 by a $C_1$-$C_6$ alkyl or a $C_1$-$C_6$ alkoxy. Specific examples of such substituents include methyl, methoxyl, hydroxylmethyl and the like.
Another especially preferred conjugate of formula (VII) (in which a=e=h=j=1 and b=c=d=f=g=i=0) is:
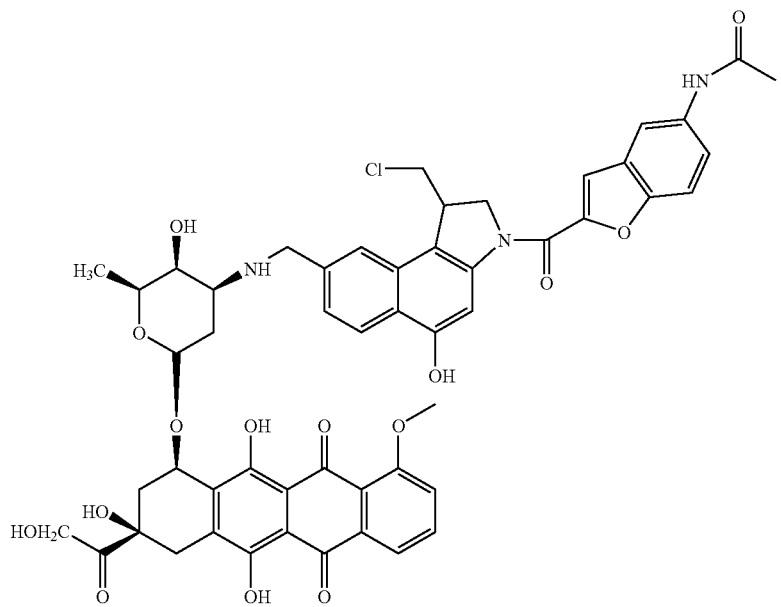

Although these two compounds do not include a polyamide sequence for minor groove binding, the CBIr and CBIf subunits have minor groove binding/recognition characteristics, so they are encompassed as DNA-intercalator—minor groove binder conjugates.

Another especially preferred conjugate of formula (VII) representing the group, of alkylator oligomers (in which e=3, a=h=j=1 and b=c=d=f=g=i=0) is:

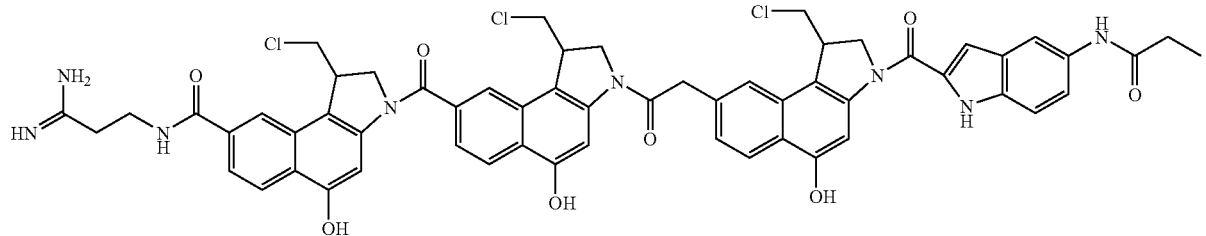

Another especially preferred conjugate of formula (VII) (in which a=b=c=d=e=f=g=i=j=1 and h=2) is:

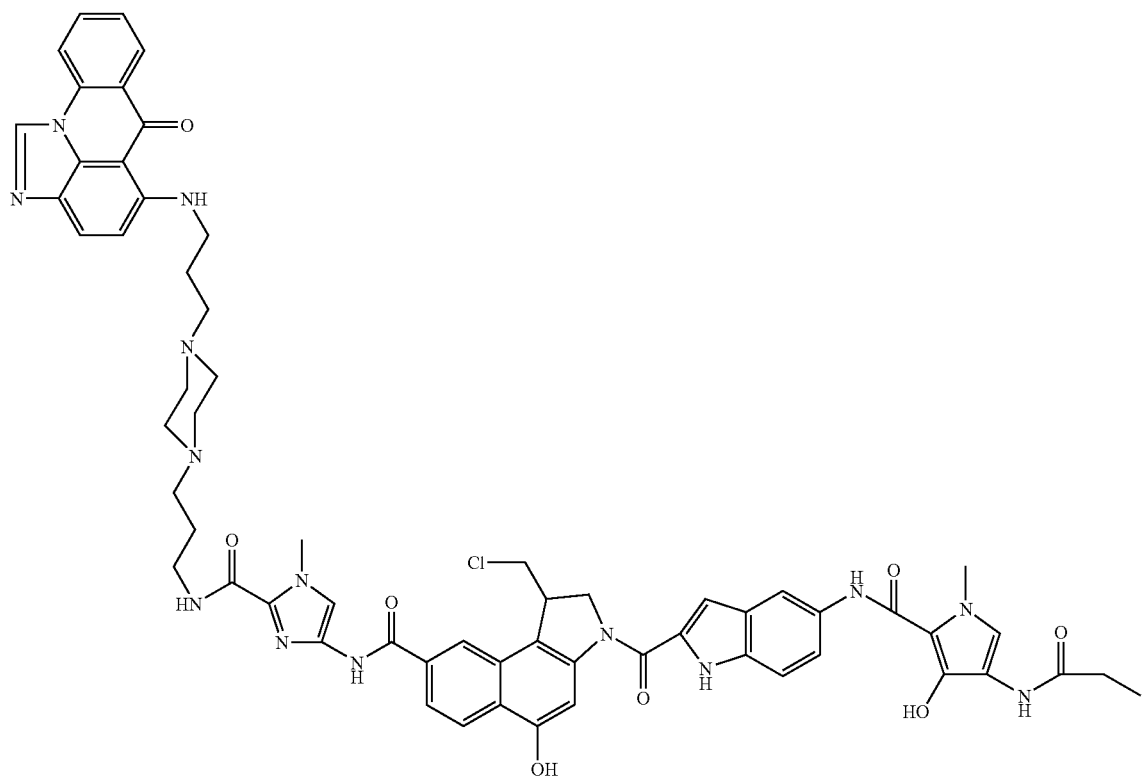

-continued
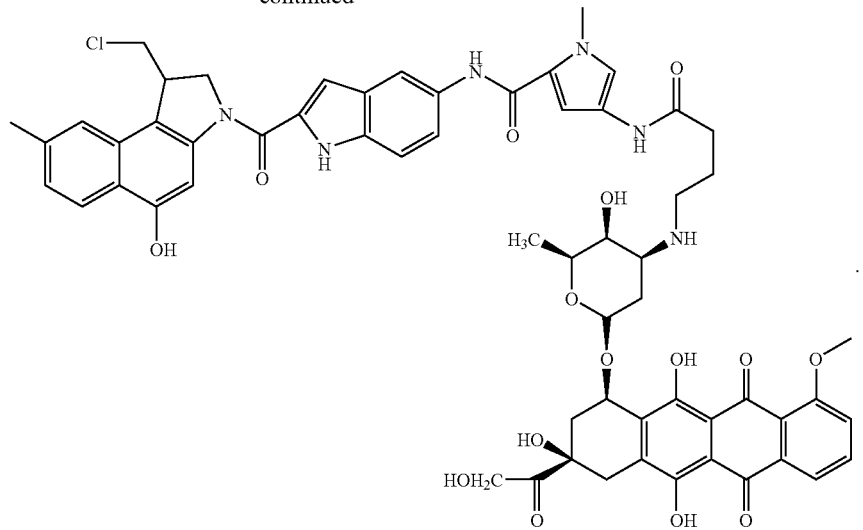
To increase the selectivity and efficacy of the conjugates of formulae (I)-(VII) double stranded hairpin polyamide group might be used in any of the conjugates. For example, the following conjugate has a folded, hairpin structure:
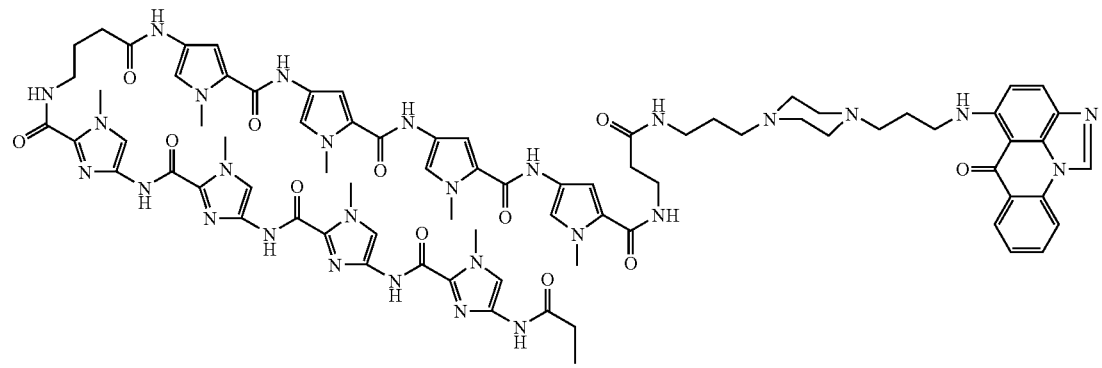
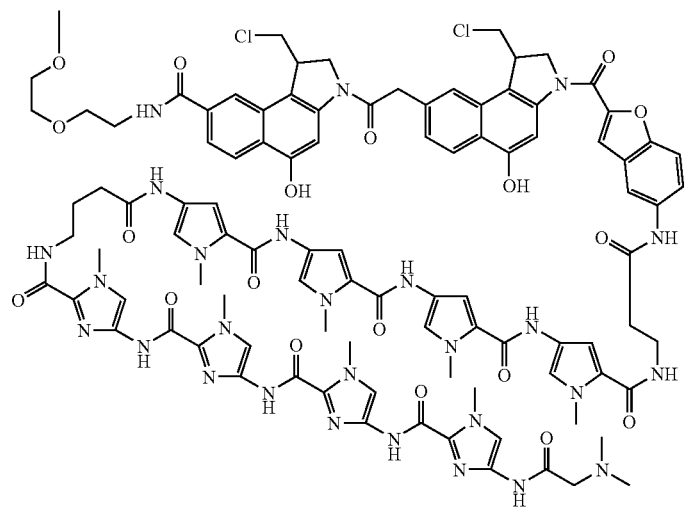

With respect to the above conjugates, a $C_1$-$C_{12}$ alkyl can be straight chain or branched chain. In addition, the $C_1$-$C_{12}$ alkyl can be optionally substituted with substituents such as, for example, hydroxy, $C_{1-12}$ alkoxy, acyloxy, halo or benzyl, acetyl, carboxyl, carboxy-$C_{1-12}$ alkyl, such as carboxymethyl, carboxyethyl, carboxy-$C_{1-12}$ alkylamido, carboxy-$C_{1-12}$ dialkylamido, carboxamido, amino, $C_{1-12}$ alkylamino, $C_{1-12}$ dialkylamino, $C_{1-12}$ alkylcarbonyl, $C_{6-30}$ arylamino, $C_{6-30}$ diarylamino, cyano, tolyl, xylyl, mesityl, anisyl, pyrrolidinyl, formyl, dioxane, thio, $C_{1-12}$ alkylthio, $C_{6-30}$ aryl, $C_{5-30}$ heteroaryl, such as pyranyl, pyrrolyl, furanyl, thiophenyl, thiazolyl, pyrazolyl, pyridinyl, or pyrimidinyl, phenoxy, benzyloxy, phenylcarbonyl, benzylcarbonyl, nitrophenyl $C_{1-12}$ trialkylsilyl, nitro, sulfonyl, nitrobenzyl, $C_{1-12}$ trialkylammonium, $C_{1-12}$ alkyl, $C_{3-8}$ cycloalkyl, tetrahydrofuranyl, tetrahydropyranyl, piperidinyl and morpholinyl. Typical examples of a $C_1$-$C_{12}$ alkyl are methyl, ethyl, n-propyl, i-propyl, n-butyl, i-butyl, s-butyl, t-butyl, pentyl, neo-pentyl, hexyl, octyl, decyl; etc.

The conjugates of formulae (I)-(VI) can be prepared by any suitable method. The examples included herein are merely exemplary methods, and the synthetic routes for the conjugates are in no way limited to these methods. Those ordinarily skilled in the art will know that the synthesis of some moieties, such as some DNA intercalators or DNA alkylators, can be prepared by methods recited in the literature.

Although not required, the conjugates are preferably prepared by heterogeneous methods using solid supports. In general, the minor groove binder oligomers are synthesized using solid-phase synthesis (see, for example, Dervan et al., *Org. Lett.*, 3: 1201-1203 (2001)). Depending on the post-solid-phase steps (e.g., coupling the minor groove binders to doxorubicin), different resins are used, such as, for example, Wang-resin, hydroxymethyl-benzoic acid resin, trityl-resin; etc.

Preferably, all of the monomers (e.g., pyrrole-, imidazole-amino acids and alkylator subunits) are introduced as protected residues (e.g., Fmoc-protected). Piperidine or piperidine/DBU typically are used to deprotect the monomers. For coupling, the monomers are preferably preactivated or activated in situ. In the case of aromatic carboxylic acids, stable benzotriazyl active esters were isolated for the coupling reaction, whereas, in the case of aliphatic carboxylic acids, various activating agents (e.g., HBTU, HATU, HOBT/DCC) were used for activation. In addition to benzotriazyl esters, aromatic carboxylic acids can be activated by oxalyl chloride in the presence of a catalytic amount of DMF and used as acyl-chlorides for coupling reactions. The alkylator residue CBIr, CBIf, or CBIa is preferably modified to form the pro-drug equivalent (seco-form) in three steps: (i) removal of the TBDMS group; (ii) converting the alcohol into a chloro group; and (iii) deprotection of the t-Butyl ether to release the phenol. The oligomer is generally cleaved from the resin using either acidolytic (e.g., Wang- or trityl resins) or nucleophilic (e.g., HMBA resin) conditions. The intercalator subunit preferably is introduced just prior to the cleavage from the resin or after the cleavage in a solution-phase step.

In another aspect, the invention provides compositions, including pharmaceutical compositions, comprising the conjugate of formula (I), (II), (III), (IV), (V), (VI), or (VII) or combinations thereof, and a carrier, alone or in further combination with other active agents, such as adjuvants and anti-cancer agents. Preferably, the pharmaceutical compositions further comprise a pharmaceutically acceptable carrier.

One ordinarily skilled in the art will appreciate that suitable methods of administering a conjugate or composition thereof to a mammal, such as a human, are known, and, although more than one route can be used to administer a particular composition, a particular route can provide a more immediate and more effective reaction than another route. If the cancer is in the form of a tumor, preferably the conjugate or composition thereof is administered intratumorally or peritumorally. Pharmaceutically acceptable carriers are also well-known in the art. The choice of carrier will be determined, in part, by the particular conjugate or composition and by the particular method used to administer the composition. Accordingly, there are a wide variety of suitable formulations of the pharmaceutical compositions of the present invention.

Formulations suitable for oral administration can consist of (a) liquid solutions, such as an effective amount of the conjugate of any of formulae (I)-(VII) dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The conjugates of the present invention, alone or in combination with other suitable components, can be made into aerosol formulations to be administered via inhalation. These aerosol formulations can be placed into pressurized acceptable propellants, such as dichlorodifluoromethane, hydrofluorocarbon (such as HFC 134a and/or 227), propane, nitrogen and the like.

Formulations suitable for parenteral administration include aqueous and non-aqueous solutions, isotonic sterile injection solutions, which can contain anti-oxidants, buffers, bacteriostats and solutes that render the formulation isotonic with the blood of the intended recipient, and aqueous and non-aqueous sterile suspensions that can include suspending agents, solubilizers, thickening agents, stabilizers and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a mammal, particularly a human, in the context of the present invention should be sufficient to effect a therapeutic response in the mammal over a reasonable time frame. The dose will be determined by the strength of the particular composition employed (taking into consideration, at least, the bioactivity of any decomposition products derived from the conjugates) and the condition of the mammal (e.g., human), as well as the body weight of the mammal (e.g., human) to be treated. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. A suitable concentration of the conjugate in pharmaceutical compositions for topical administration is 0.05 to 15% (by weight), preferably 0.02 to 5%, and more preferably 0.1 to 3%.

The conjugates of any of formulae (I)-(VI) or compositions thereof are useful for treating a mammal, such as a human, for cancer. The method comprises administering to the mammal, e.g., human, a cancer-treatment effective amount of a conjugate of any of formulae (I)-(VII) or a composition thereof, whereupon the mammal is treated for cancer. The treatment can be prophylactic or therapeutic. By "prophylactic" is meant any degree in inhibition of the onset of cancer, including complete inhibition. By "therapeutic" is meant any degree in inhibition of the growth or metastasis of the cancer in the mammal (e.g., human).

The method can be used in combination with other known treatment methods, such as radiation, surgery, or the administration of other active agents, such as adjuvants or other anti-cancer agents and their prodrugs. Examples of cyotoxic agents and their prodrugs include genistein, okadaic acid, 1-β-D-arabinofuranosyl-cytosine, arabinofuranosyl-5-azacytosine, cisplatin, carboplatin, actinomycin D, asparaginase, bis-chloro-ethyl-nitroso-urea, bleomycin, chlorambucil, cyclohexyl-chloro-ethyl-nitroso-urea, cytosine arabinoside, daunomycin, etoposide, hydroxyurea, melphalan, mercaptopurine, mitomycin C, nitrogen mustard, procarbazine, teniposide, thioguanine, thiotepa, vincristine, 5-fluorouracil, 5-fluorocytosine, adriamycin, cyclophosphamide, methotrexate, vinblastine, doxorubicin, leucovorin, taxol, anti-estrogen agents such as tamoxifen, intracellular antibodies against oncogenes, the flavonol quercetin, Guan-mu-tong extract, retinoids such as fenretinide, nontoxid retinoid analogues such as N-(4-hydroxyphenyl)-retinamide (HPR), and monoterpenes such as limonene, perillyl alcohol and sobrerol.

The method of treating cancer with a conjugate of any of formulae (I)-(VII) or composition thereof can be combined with still other methods of prophylactic and therapeutic treatment. Such methods include those that target destruction of cancer cells, e.g., by targeting of cell-surface markers, receptor ligands, e.g., ligands to gastrin-releasing peptide-like receptors, tumor-associated antigens, e.g., the 57 kD cytokeratin or the antigen recognized by the monoclonal antibody GB24, the extracellular matrix glycoprotein tamascin, DNA replication, the transcription of genes whose protein products are necessary for the survival of the cancer, e.g., proteins involved in signal transduction, growth factor receptors, nuclear oncoproteins, antagonists of apoptosis, antagonists of tumor suppressors, and proteins involved in DNA repair processes, antisense oncogenes such as c-fos, homeobox genes that are expressed in cancer cells but not normal cells, tumor-infiltrating lymphocytes that express cytokines, RGD-containing peptides and proteins, which are administered following surgery, lipophilic drug-containing liposomes to which are covalendy conjugated monoclonal antibodies for targeting to cancer cells, low fat diet, moderate physical exercise and hormonal modulation. For prostate cancer, anti-testosterone agents can be used as well as an inhibitor of cellular proliferation produced by prostatic stromal cells and C-CAM, an epithelial cell adhesion molecule.

The conjugates of any of formulae (I)-(VII) preferably are useful for targeting coding regions or control regions of genes, such as promoters or enhancers, and inhibiting transcription. Cancers that are suitable to treatment with conjugates of the present invention include those in which specific genes are known to be mutated and/or over-expressed and necessary for the survival of the cancer cell. Preferably, the molecular pathogenesis of the cancer involves one or more potential molecular targets: (i) molecules involved in signal transduction (e.g., K-Ras); (ii) growth factor receptors (e.g., Her-2-Neu); (iii) nuclear oncoproteins (e.g., c-Myc); (iv) antagonists of apoptosis (e.g., BCL2); and (v) antagonists of tumor suppressors (e.g., MDM2); (vi) DNA repair processes; and (vii) DNA transcription and replication. For instance, typical cancers that are to be treated in conduction with the conjugates and compositions of the present invention incude breast cancer, metastatic melanoma, follicular thyroid carcinoma, colorectal cancer, pancreatic cancer, leukemias, such as myeloid leukemia, prostate cancer, hepatic cancer, hepatocellular carcinoma, cholangiocarcinoma, cervical and ovarian cancer, cancers of glial origin and renal cancer.

EXAMPLES

The following examples further illustrate the invention but, of course, should not be construed as in any way limiting its scope.

The following abbreviations are used herein:
BOC or Boc i-Butyloxycarbonyl,
Bn Benzyl,
Bt 1H-Benztriazol-1-yl,
'Bu t-Butyl,
DBU 1,8-Diazabicyclo[5.4.0]undec-7-ene,
DCC 1,3-Dicyclohexylcarbodiimide,
DCM Dichloromethane,
DIPEA Diisopropylethylamine,
DPPA Diphenylphosphoryl azide,
FMOC or Fmoc 9-Fluorenylmethoxycarbonyl,
FmocCl 9-Fluorenylmethoxycarbonylchloride,
Fmoc-Im-OBt (1H-Benzotriazole-1-yl) 4-(9-fluorenylmethoxycarbonyl)amino-1-methylimidazole-2-carboxylate,
Fmoc-Py-OBt (1H-Benzotriazole-1-yl) 4-(9-fluorenylmethoxycarbonyl)amino-1-methylpyrrole-2-carboxylate,
HATU 2-(1H-7-Azabenzotriazole-1-yl)-1,1,3,3-tetramethyluronium hexafluorophosphate,
HBTU 2(1H-Benzotriazole-1-yl)-1,1,3,3-tetramethyluronium hexafluorophosphate,
HFIP Hexafluoroisopropanol,
HMBA Hydroxymethylbenzoicacid,
HOAt N-Hydroxy-7-azabenzotriazole,
HOBt N-Hydroxybenzotriazole,
Im Imidazole
NIS N-Iodosuccinimide,
NMP N-Methylpyrrolidone,
Py pyrrole,
OBt 1-oxy-benztriazol,
TBDMS t-Butyldimethylsilyl,
TBDMSCl t-Butyldimethylsilylchloride,
TBTH Tributyltinhydride,
t-BuOH t-Butanol,
TEMPO 2,2,6,6-tetramethyl-1-piperidinyloxy,
TFA Trifluoroacetic acid,
TsOH p-Toluenesulfonic acid,
WSC 1-Ethyl-3(3'-dimethylaminopropyl)carbodiimide. HCl (water-soluble carbodiimide), and
solvent (m×n) washing the resin with a solvent for 'm' times during 'n' min.

Example 1

This examples describes the synthesis of (1-(chloromethyl)-5-hydroxy-1,2-dihydro-3H-benz[e]indole-8-carboxylic acid) ("CBIr"), a rigid DNA alkylator (FIG. 1).

The synthesis procedure for compound 1 {5-(Benzyloxy)-3-(tert-butyloxycarbonyl)-8-cyano-1-[(2',2',6',6'-tetramethylpiperidino)oxy]methyl-1,2-dihydro-3H-benz[e]indole} followed that described by Boger (*J. Org. Chem.* 61: 4894-4912 (1996)). The subsequent synthetic steps were developed to achieve the synthesis of 8 and 9. These steps are described below.

Benzyl 5-(benzyloxy)-3-tert-butyloxycarbonyl)-1-[(2',2',6',6'-tetramethylpiperidino)oxy]methyl-1,2-dihydro-3H-benz[e]indole-8-carboxylate (2)

A solution of 1 (1.72 g, 2.33 mmol, 1.0 equiv) in 2-methoxyethanol (6 mL) in a round-bottom flask was treated with CsOH (monohydrate, 1.96 g, 11.65 mmol, 5.0 equiv) and brought to reflux under a $N_2$ stream. After 30 min, the temperature was decreased to 105° C. and the reaction mixture was stirred for 14 hr. At this point, no more ammonia was detected by indicator paper in the effluxed $N_2$. The reaction mixture was then cooled to 25° C., and the volatiles were removed in vacuo. The dark brown solid residue was dried overnight in high vacuum. Solid $CO_2$ was added to the solution of the crude reaction product in acetonitrile (10 mL) at 25° C. The mixture was cooled to 0° C., treated with benzyl bromide (0.554 mL, 4.66 mmol, 2.0 equiv) and stirred for 1 hr. The reaction mixture then was warmed to 50° C. and was stirred for 30 min and cooled to 25° C. 10% aqueous $KHSO_4$ and EtOAc were added, and the aqueous layer was extracted with EtOAc, and the combined organic extract was washed with water and saturated aqueous NaCl, dried ($MgSO_4$), and concentrated in vacuo. Flash chromatography ($SiO_2$, 2.5×12 cm, 0-25% EtOAc-hexane gradient) provided 2 (1.29 g, 82%) as an off-white solid.

ES-MS m/z 679.3 (M+H$^+$, $C_{42}H_{51}N_2O_6$ requires m/z 679.3747).

Benzyl 5(benzyloxy)-3-(9H-fluoren-9-ylmethoxycarbonyl)-1-[(2',2',6',6'-tetramethylpiperidino)oxy]methyl-1,2-dihydro-3H-benz[e]indole-8-carboxylate (3)

A solution of 2 (1.15 g, 1.69 mM) in DCM (4 mL) was cooled to 0° C. Aqueous TFA (90%; 15 mL) was cooled to 0° C. The TFA solution was added to the DCM solution dropwise with stirring for 30 min. The solution was then slowly warmed up to 25° C. and was stirred for 20 min. The volatiles were removed in vacuo. The trifluoroacetate salt was dried for 3 hr in high vacuum and dissolved in anhydrous DMF (8 mL) under argon. The solution was cooled to 0° C. and treated with DIPEA (1.18 mL, 6.76 mM, 4.0 equiv), and a solution of Fmoc-Cl (0.456 g, 1.77 mM, 1.05 equiv), in anhydrous DMF was added during the period of 10 min. The reaction mixture was allowed to warm up to 25° C. The DMF was evaporated in vacuo, and the solid residue was dissolved in EtOAc. The solution was extracted with $H_2O$, and the combined aqueous extract was re-extracted with EtOAc. The combined organic extract was washed with water and saturated aqueous NaCl, dried ($MgSO_4$), and concentrated in vacuo. Flash chromatography ($SiO_2$, 2.5×12 cm, 0-25% EtOAc-hexane gradient) provided 3 (1.23 g, 91%) as an off-white solid.

ES-MS m/z 801.4 (M+H$^+$, $C_{52}H_{53}N_2O_6$ requires m/z 801.3903).

Benzyl 5-(benzyloxy)-3-(9H-fluoren-9-ylmethoxycarbonyl)-1-(hydroxymethyl)-1,2-dihydro-3H-benz[e]indole-8-carboxylate (4)

A solution of 3 (1.05 g, 1.31 mmol, 1.0 equiv) in THF-HOAc (3:1, 30 mL) under flowing $N_2$ was treated with activated Zn powder (3.43 g, 40 equiv) and warmed to 75° C. It was then treated with $H_2O$ (8 mL), and the mixture was stirred for 6 hr. The Zn powder was removed by filtration and washed with THF (10 mL) 3 times. The combined filtrate was evaporated in vacuo and dissolved in EtOAc. The EtOAc solution was washed with 10% aqueous $KHSO_4$, water and saturated aqueous NaCl, dried ($MgSO_4$), and concentrated in vacuo. Flash chromatography ($SiO_2$, 2.5×12 cm, 10-40% EtOAc-hexane gradient) provided 4 (746 mg, 86%) as an off-white solid.

ES-MS m/z 662.2 (M+H$^+$, $C_{43}H_{36}N_1O_6$ requires m/z 662.2542).

Benzyl 5-(benzyloxy)-3-(9H-fluoren-9-ylmethoxycarbonyl)-(tert-butyl-dimethyl-silanyloxymethyl)-1,2-dihydro-3H-benz[e]indole-8-carboxylate (5)

A solution of 5 (720 mg, 1.09 mM, 1.0 equiv) in anhydrous DMF (3 mL) under argon was cooled to 0° C. treated with DIPEA (0.492 mL, 2.83 mM, 2.6 equiv) and with a solution of TBDMS-Cl (214 mg, 1.417 mM, 1.3 equiv) in anhydrous DMF (1 mL). The reaction mixture was then slowly warmed up to 25° C. and was stirred for 20 min. The volatiles were removed in vacuo and the solid residue was dissolved in EtOAc. The solution was extracted with $H_2O$ twice, and the combined aqueous extract was re-extracted with EtOAc. The combined organic extract was washed with water and saturated aqueous NaCl, dried ($MgSO_4$), and concentrated in vacuo. Flash chromatography ($SiO_2$, 2.5×12 cm, 0-20% EtOAc-hexane gradient) provided 5 (795 mg, 94%) as a light yellow solid.

ES-MS m/z 776.3 (M+H$^+$, $C_{49}H_{49}NO_6Si$ requires m/z 776.3407).

5-(tert-Butyl-dimethyl-silanyloxy)-3-(9H-fluoren-9-ylmethoxycarbonyl)-1-(tert-butyl-dimethyl-silanyloxymethyl)-1,2-dihydro-3H-benz[e]indole-8-carboxylic Acid (7)

A solution of 5 (750 mg, 0.97 mM, 1 equiv) in anhydrous EtOAc/EtOH (1:1 v/v, 10 mL) was treated with a slurry of 10% Pd/C (250 mg) in anhydrous EtOH (5 mL). The resulting slurry was degassed with a stream of $N_2$ for 1 min. The reaction mixture was placed under an atmosphere of $H_2$ and stirred for 6 hr. THF (50 mL) was added to the reaction mixture and filtered through Celite. The Celite was washed with THF 5 times (15 mL each). The volatiles of the combined filtrates were removed in vacuo. The resulting slurry was dried under high vacuum over night. The debenzylated intermediate 6 was dissolved in anhydrous DMF (5 mL), stirred, cooled to 0° C., and treated with DIPEA (0.843 mL, 4.85 mM, 5 equiv) and a solution of TBDMS-Cl (365 mg, 2.43 mM, 2.5 equiv) in anhydrous DMF (1 mL). The reaction mixture was then slowly warmed to 25° C. and stirred for 40 min. The solvents were removed in vacuo, and the solid residue was dissolved in 30 mL of THF-AcOH (3:1) and stirred at room temperature. Water (10 mL) was added to the reaction mixture, and it was stirred for 1 hr. The volatiles were removed in vacuo and the solid residue was dissolved in EtOAc. The solution was extracted with $H_2O$ twice, and the combined aqueous extract was re-extracted with EtOAc. The combined organic extract was washed with water and saturated aqueous NaCl, dried ($MgSO_4$), and concentrated in vacuo. Flash chromatography ($SiO_2$, 2.5×12 cm, 0-20% EtOAc-hexane gradient) provided 6(599 mg, 87%) as a light yellow solid.

ES-MS m/z 710.3 (M+H$^+$, $C_{41}H_{51}NO_6Si_2$ requires m/z 710.3333).

Activation of 7

Method A: 71 mg of 7 (0.1 mM, 1.0 equiv) were dissolved in anhydrous DMF. The solution was treated with 14 mg of HOBt (0.105 mM, 1.05 equiv) and 22 mg of DCC (0.105 mM, 1.05 equiv), and stirred at room temperature for 20 min, which resulted in the formation of 8.

Method B: 71 mg of 6 (0.1 mM, 1.0 equiv) were dissolved in anhydrous DMF. The solution was treated with oxalyl chloride (22 μL, 0.25 mM, 2.5 eq) and 1 μL of DMF. The reaction mixture was stirred for 12 hr, which resulted in the formation of 9.

Example 2

Figure 2:
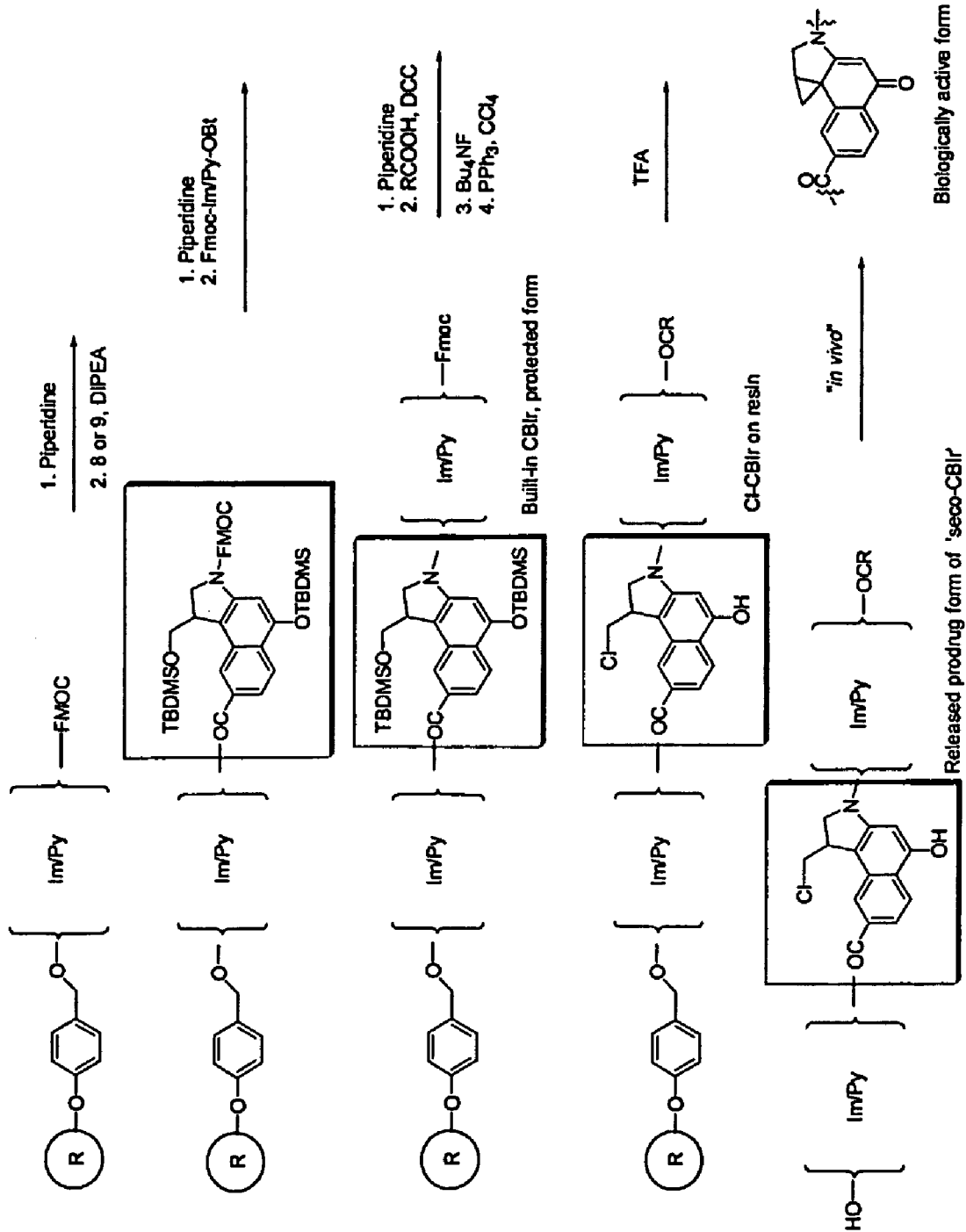
FIG. 2 depicts the convergent solid phase synthesis of a conjugate comprising {1-(chloromethyl)-5-hydroxy-1,2-dihydro-3H-benz[e]indole-8-carboxylic acid} ("CBIr"), a rigid DNA alkylator.

This examples describes the convergent solid phase synthesis of a conjugate comprising {1-(chloromethyl)-5-hydroxy-1,2-dihydro-3H-benz[e]indole-8-carboxylic acid} ("CBIr"), a rigid DNA alkylator (FIG. 2).

Glycinol 2-chlorotrityl resin (Novabiochem, San Diego, Calif.) was used to synthesize the following polyamide sequence: Propanoyl-Py-Py-CBIr-Im-Im-glycinol. After swelling for 1 hr in NMP, the resin was drained, Fmoc-Im-OBt (3 eq) and DIPEA (5 eq) were added and the mixture was agitated for 2 hr at 40° C. The resin was washed with NMP 4 times. The Fmoc group was removed by two subsequent treatments of 40% (v/v) piperidine in NMP (15 min each) then the resin was extensively washed with NMP (6×2 min). The above-described 'coupling-washing-deprotection-washing' cycle was repeated 4 times to couple the following residues: Fmoc-Im-OBt, Fmoc-CBIr-OBt, Fmoc-Py-OBt, Fmoc-Py-OBt. To terminate the N-terminal amino group, propionic anhydride (2 eq) and DIPEA (4 eq) were added and the mixture was agitated for 30 min. After washing with NMP (3×3 min) and DCM (3×3 min), the TMDMS groups were removed by TBAF (0.1 M solution in THF, 2×10 min treatment) and the alcohol was chlorinated using PPh3 (2 eq) and CCl4 (2 eq) for 4 hr. The polyamide was cleaved by two subsequent treatments of 30% (v/v) HFIP in DCM (30 min each). The filtered cleavage mixtures were combined and both HFIP and DCM were removed under reduced pressure. The product was analyzed by analytical HPLC and ES-MS. and purified by preparative HPLC.

Example 3

Figure 3:
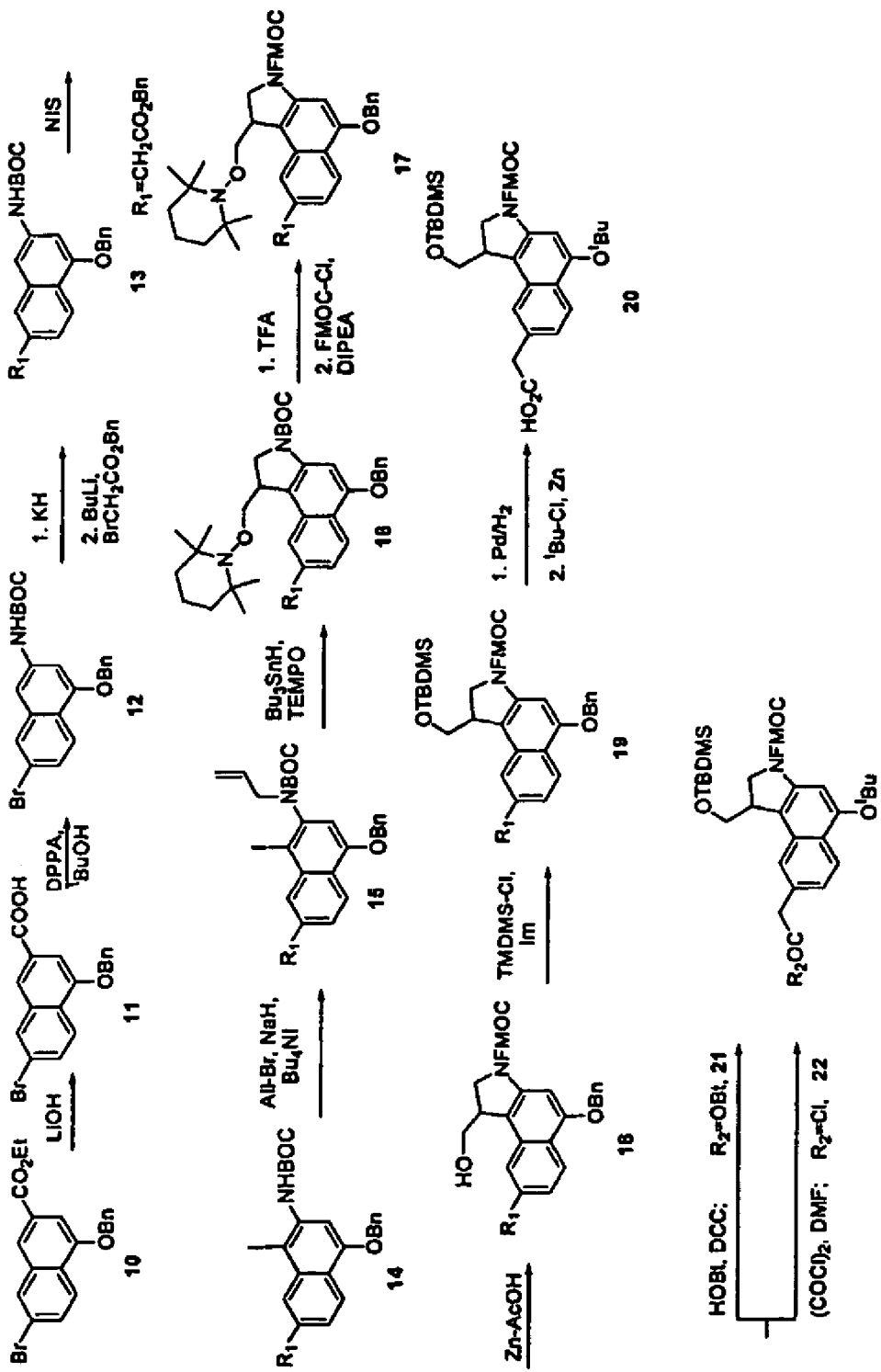
FIG. 3 depicts the synthetic scheme of 2-{1-(chloromethyl)-5-hydroxy-1,2-dihydro-3H-benz[e]indol-8-yl}acetic acid ("CBIf"), a flexible DNA alkylator.

This examples describes the synthetic scheme of 2-{1-chloromethyl)-5-hydroxy-1,2-dihydro-3H-benz[e]indol-8-yl}acetic acid ("CBIf"), a flexible DNA alkylator (FIG. 3).

The synthesis until compound 10 follows the same procedure described by Boger (*J. Org. Chem.*, 61: 48944912 (1996)). Mild alkaline hydrolysis of 10 using LiOH provided the acid 11. Curtius rearrangement using DPPA in t-BuOH formed the protected amine 12, in which the Br was exchanged to Li. Compound 21 was reacted with t-butyl bromoacetate to produce 13. During this conversion, the proton of the urethane was masked as its potassium salt using KH. Iodination of 14 by NIS in the presence of a catalytic amount of TsOH followed by allylation with allyl bromide and NaH resulted in 15. Radical cyclization of 16 was carried out using TBTH and TEMPO and resulted in 17. In order to synthesize solid-phase compatible, amino-acid-like compound 21 or 22, all the protecting groups were removed and three different protecting groups were introduced in the following order: (i) removal of the BOC and t-Bu ($R^1$ in FIG. 3) using HCl in dioxane; (ii) Fmoc protection of the secondary amine; (iii) freeing the alcoholic OH group by Zn/AcOH treatment; (iv) reprotection of the hydroxyl group as the TBDMS ether, (v) hydrogenolysis of the benzyl group; and (vi) protection of the resulting phenol as the t-Bu ether provided 20. Before solid-phase application, 20 was activated to the benzotriazyl active ester (21) or to the acyl chloride (22).

Example 4

Figure 4:
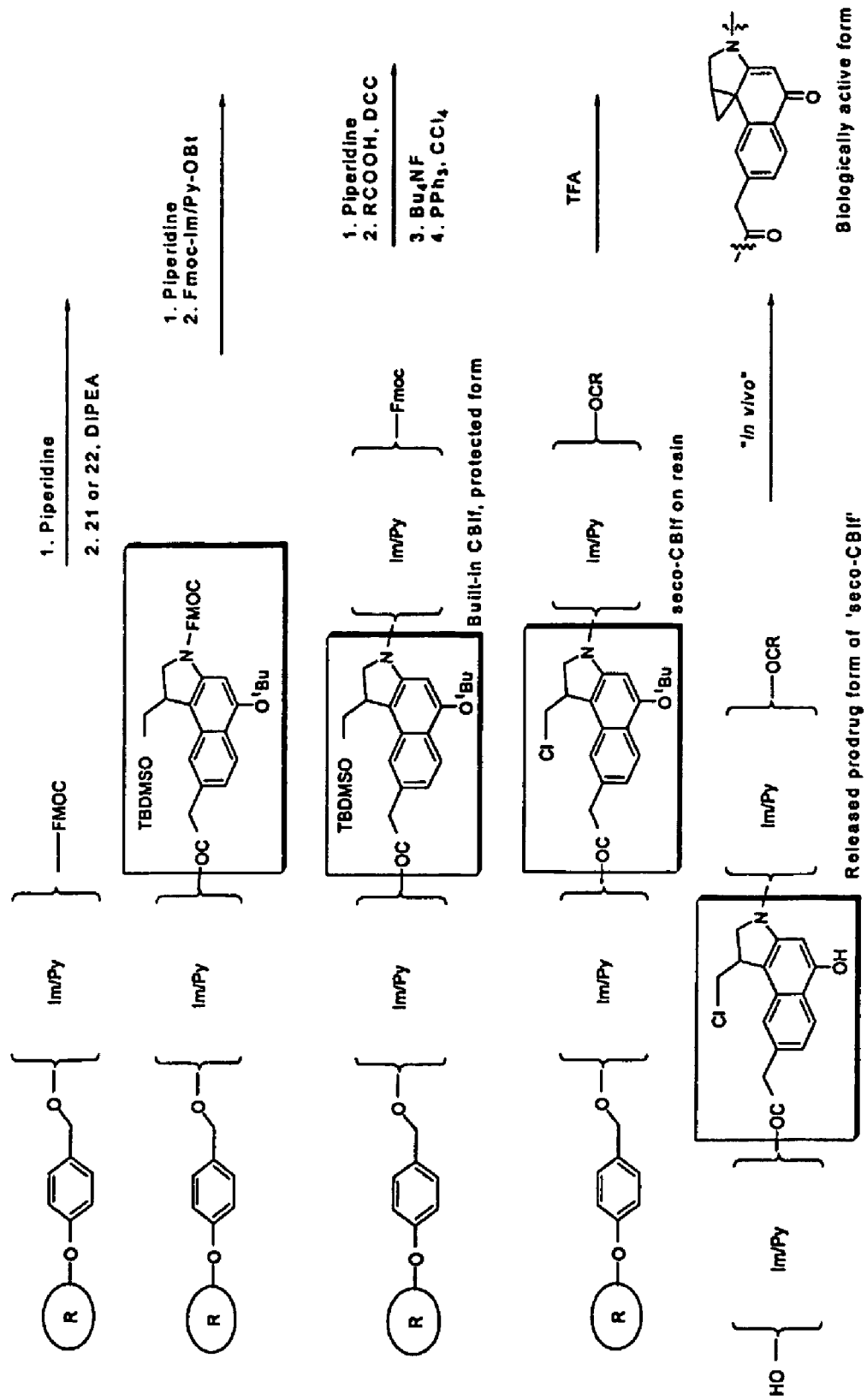
FIG. 4 depicts the convergent solid phase synthesis of a conjugate comprising 2-{1-(chloromethyl)-5-hydroxy-1,2-dihydro-3H-benz[e]indol-8-yl}acetic acid ("CBWIf"), a flexible DNA alkylator.
Figure 5:
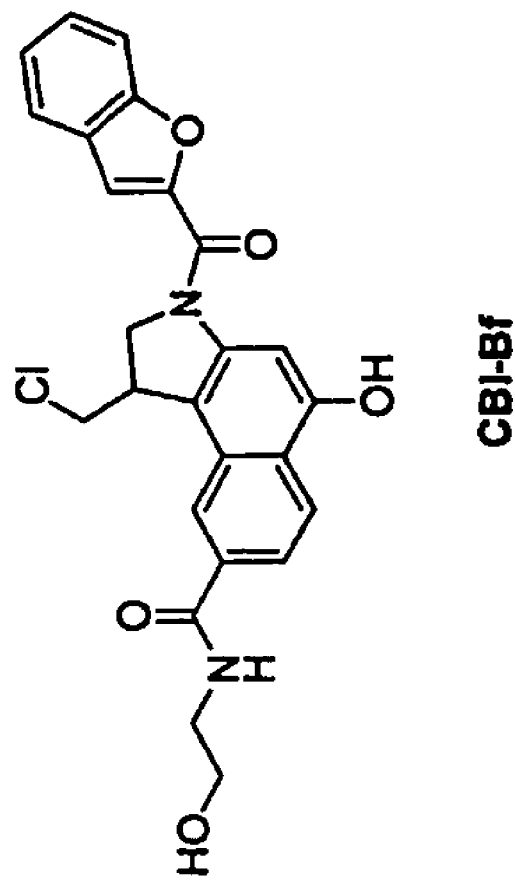
FIG. 5 shows the structures of CBI-AM and CBI-Bf.
Figure 5:
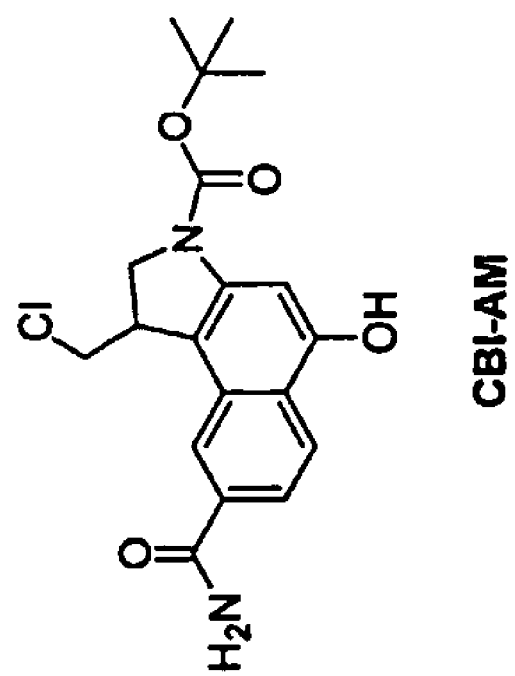
Figure 6A:
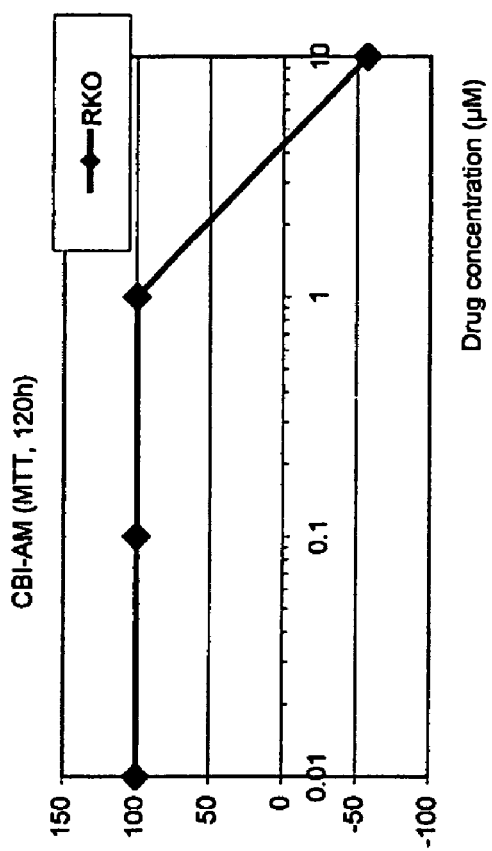
FIG. 6A is a graph of % cell growth vs. drug concentration (μM) for CBI-AM in an MTT assay at 120 hr.
Figure 6B:
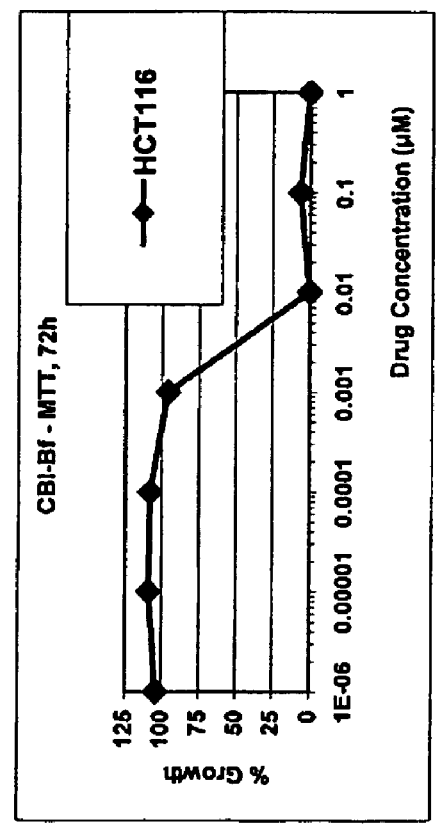
FIG. 6B is a graph of % growth vs. drug concentration (μM) for CBI-BF in an MTT assay at 72 hr.

This examples describes the convergent solid phase synthesis of a conjugate comprising 2-{1-(chloromethyl)-5-hydroxy-1,2-dihydro-3H-benz[e]indol-8-yl}acetic acid ("CBIf"), a flexible DNA alkylator (FIG. 4).

Glycinol 2-chlorotrityl resin Novabiochem, San Diego, Calif.) was used to synthesize the following polyamide sequence: Propanoyl-Py-Py-CBIf-Im-Im-glycinol. After swelling for 1 hr in NMP, the resin was drained, Fmoc-Im-OBt (3 eq) and DIPEA (5 eq) were added and the mixture was agitated for 2 hr at 40° C. The resin was washed with NMP 4 times. The Fmoc group was removed by two subsequent treatments of 40% (v/v) piperidine in NMP (15 min each) then the resin was extensively washed with NMP (6×2 min). The above-described 'coupling-washing-deprotection-washing' cycle was repeated 4 times to couple the following residues: Fmoc-Im-OBt, Fmoc-CBIf-OBt, Fmoc-Py-OBt, Fmoc-Py-OBt. To terminate the N-terminal amino group, propionic anhydride (2 eq) and DIPEA (4 eq) were added, and the mixture was agitated for 30 min. After washing with NMP (3×3 min) and DCM (3×3 min), the TMDMS groups were removed by TBAF (0.1 M solution in THF, 2×10 min treatment) and the alcohol was chlorinated using PPh3 (2 eq) and CCl4 (2 eq) for 4 hr. The polyamide was cleaved by two subsequent treatments of 30% (v/v) HFIP in DCM (30 min each). The filtered cleavage mixtures were combined, and both HFIP and DCM were removed under reduced pressure. The product was analyzed by analytical HPLC and ES-MS and purified by preparative HPLC.

Example 5

This example demonstrates the cytotoxic effect of the present inventive compounds against cancerous cells.

In order to determine the cytotoxicity of the compounds, "Cell Titer 96" non-radioactive cell proliferation assay (Mossman, *J. Immunol. Meth.* 65:55 (1983)) was used. Preliminary cytotoxicity data for CBI-amide against human colon cancer cell line show that it is 3 orders of magnitude (1000-fold) less active than the CBI-Bf molecule in HCT116 human colon cancer cell line. The two cell lines have a very similar response to these types of drugs. The much higher activity of CBI-Bf illustrates the necessity of extension of the CBI residue by the bicyclic benzofuran. Other bicyclic or tricyclic residues that satisfy certain geometric requirements are also effective promoters of activity of CBI. This result indicates that a CBI-Bf or a similarly activated CBI can be used as an embedded alkylator in a DNA-sequence selective minor groove binder.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A conjugate of formula:

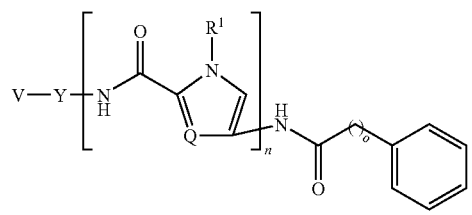

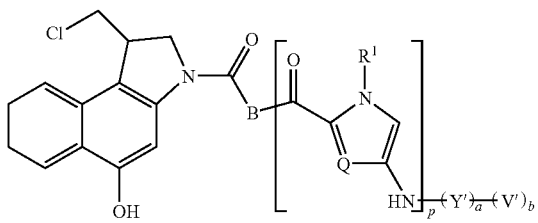

wherein

V and V' are the same or different and each is doxorubicin, daunorubicin, imidazoacridone, 3-nitrophthalamide or 3-aminophthalamide, B is a heteroaromatic residue comprising a subunit of 4-amino-1-methylpyrrole-2-carboxylic acid, 4-amino-1-methylimidazole-2-carboxylic acid, 4-amino-1methyl-3-hydroxypyrrole-2-carboxylic acid, γ-amino-butyric acid, α,γ-diamino-butyric acid, glutamic acid 8-amino-3,6-dioxanioic acid, β-alanine, 4-amino-benzoic acid, 3-amino-benzoic acid, 2-aminothiazole-5-carboxylic acid, 4-aminothiophene-2-carboxylic acid, 5-aminobenzthiophene-2-carboxylic acid, 5-aminobenzoxazole-2-carboxylic acid, or 5-aminobenzimidazole-2-carboxylic acid, Y and Y' are the same or different and each is a bifunctional linker comprising a group selected from the group consisting of amino, $C_1$-$C_{12}$ alkylamino, $C_1$-$C_{12}$ dialkylamino, cycloalkylamino, piperazinyl, piperidinyl, pyrazinyl, purinyl, pyridazinyl, pyrrolidinyl, oxazolyl, isooxazolyl, quinolinyl, isoquinolinyl, byrimidinyl, morpholinyl, thiazolyl, isothiazolyl, quinoxalinyl, quinazolinyl, pyrrolyl, imidazolyl and an amino acid residue, in each repeat unit designated by n or p, Q is independently N or $CR^2$, $R^1$ and $R^2$ are the same or different and each is selected from the group consisting of hydrogen, $C_1$-$C_{12}$ alkyl, hydroxy, and halogen, n and p are independently 1 to 6, o is 0 or 1, and a and b are independently 0 to 1.

2. The conjugate of claim 1, wherein the linker Y or Y' comprises N,N'-bis(aminopropyl)piperazine, N,N'-bis(aminopropyl)methylamine, 8-amino-3,6-dioxaoctanoic acid, spermidine or ⊖-alanine.

3. The conjugate of claim 1, wherein Q is N.

4. The conjugate of claim 1, wherein $R^1$ is $C_1$-$C_{12}$ alkyl.

5. The conjugate of claim 4, wherein $R^1$ is methyl.

6. The conjugate of claim 1, wherein n is 4 or 5.

7. The conjugate of claim 6, wherein n is 4.

8. The conjugate of claim 1, wherein o is 0.

9. The conjugate of claim 1, wherein V and V' are the same or different and each is doxorubicin or daunonibicin.

10. A conjugate of formula:

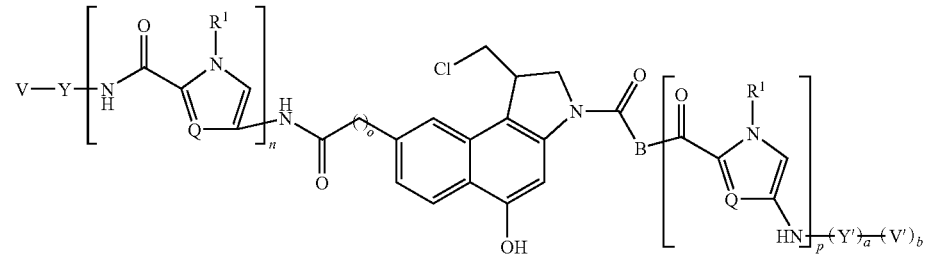

wherein

V and V' are the same or different and each is a substituted doxorubicin, a substituted daunorubicin. imidazoacridone. a substituted 3-nitrophthalamide or a substituted 3-aminophthalamide.

wherein the substituent is selected from the group consisting of $C_{1-12}$ alkyl, $C_{3-8}$ cycloalkyl, $C_{6-30}$ aryl, $C_{5-30}$ heteroaryl, tolyl, xylyl, mesityl, anisyl, hydroxy, $C_{1-12}$ alkoxy, phenoxy, benzyloxy, acyloxy, halogen, cyano, benzyl, formyl, phenylcarbonyl, benzylcarbonyl, acetyl, carboxyl, carboxy-$C_{1-12}$ alkyl, carboxy-$C_{1-12}$ alkylamido, carboxy-$C_{1-12}$ dialkylamido, carboxamido, amino, $C_{1-12}$ alkylamino, $C_{1-12}$ dialkylamino, $C_{1-12}$ alkylcarbonyl, $C_{6-30}$ arylamino, $C_{6-30}$ diarylamino, mercapto, $C_{1-12}$ alkylthio, nitro, nitrophenyl, nitrobenzyl, $C_{1-12}$ trialkylsilyl, sulfonyl, $C_{1-12}$ trialkylammonium, pyrrolidinyl, dioxanyl, tetrahydrofuranyl, tetrahydropyranyl, piperidinyl, and morpholinyl, B is a heteroaromatic residue comprising a subunit of 4-amino-1-methylpyrrole-2-carboxylic acid, 4-amino-1-methylimidazole-2-carboxylic acid, 4-amino-1methyl-3-hydroxypyrrole-2-carboxylic acid, γ-amino-butyric acid, α,γ-diamino-butyric acid, glutamic acid, 8-amino-3,6-dioxanioic acid, β-alanine, 4-amino-benzoic acid, 3-amino-benzoic acid, 2-aminothiazole-5-carboxylic acid, 4-aminothiophene-2-carboxylic acid, 5- aminobenzthiophene-2-carboxylic acid, 5-aminobenzoxazole-2-carboxylic acid, or 5-aminobenzimidazole-2-carboxylic acid, Y and Y' are the same or different and each is a bifunctional linker comprising a group selected from the group consisting of amino, $C_1$-$C_{12}$ alkylamino, $C_1$-$C_{12}$ dialkylamino, cycloalkylamino, piperazinyl, piperidinyl, pyrazinyl, purinyl, pyridazinyl, pyrrolidinyl, oxazolyl, isooxazolyl, quinolinyl, isoquinolinyl, byrimidinyl, morpholinyl, thiazolyl, isothiazolyl, quinoxalinyl, quinazolinyl, pyrrolyl, imidazolyl and an amino acid residue, in each repeat unit designated by n or p, Q is independently N or $CR^2$, $R^1$ and $R^2$ are the same or different and each is selected from the group consisting of hydrogen, $C_1$-$C_{12}$ alkyl, hydroxy, and halogen, n and p are independently 1 to 6, o is 0 or 1, and a and b are independently 0 to 1.

11. A conjugate of formula:

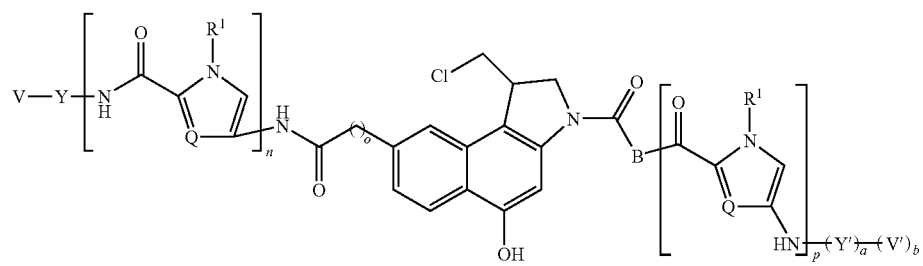

wherein

V and V' are the same or different and each is doxorubicin, daunorubicin, or imidazoacridone, B is a heteroaromatic residue comprising a subunit of 2-carbonyl-1H-indole or 2-carbonyl-benzofuran, Y and Y' are the same or different and each is a bifunctional linker comprising a group selected from the group consisting of amino, $C_1$-$C_{12}$ alkylamino, $C_1$-$C_{12}$ dialkylamino, cycloalkylamino, piperazinyl, piperidinyl, pyrazinyl, purinyl, pyridazinyl, pyrrolidinyl, oxazolyl, isooxazolyl, quinolinyl, isoquinolinyl, byrimidinyl, morpholinyl, thiazolyl, isothiazolyl, quinoxalinyl, quinazolinyl, pyrrolyl, imidazolyl and an amino acid residue, in each repeat unit designated by n or p, Q is independently N or $CR^2$, $R^1$ and $R^2$ are the same or different and each is selected from the group consisting of hydrogen, $C_1$-$C_{12}$ alkyl, hydroxy, and halogen, n and p are independently 1 to 6, o is 0 or 1, and a and b are independently 0 to 1.

12. The conjugate of claim 11, which is
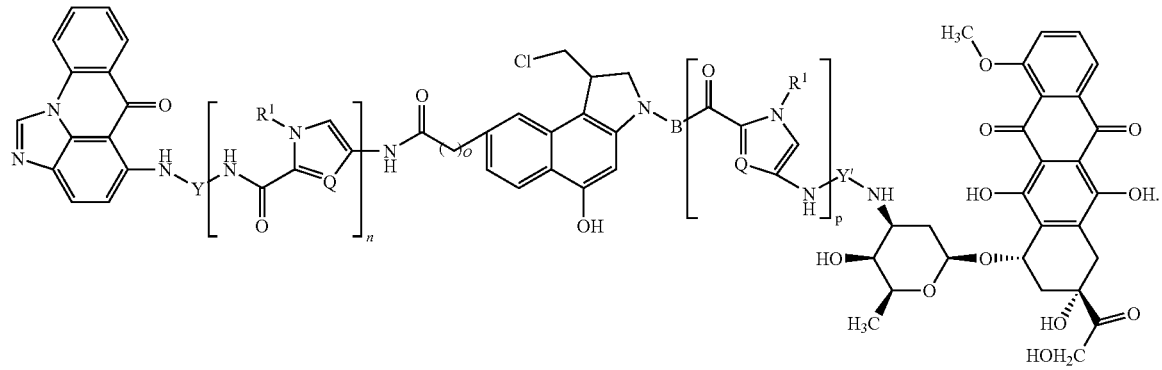
13. The conjugate of claim 12, which is
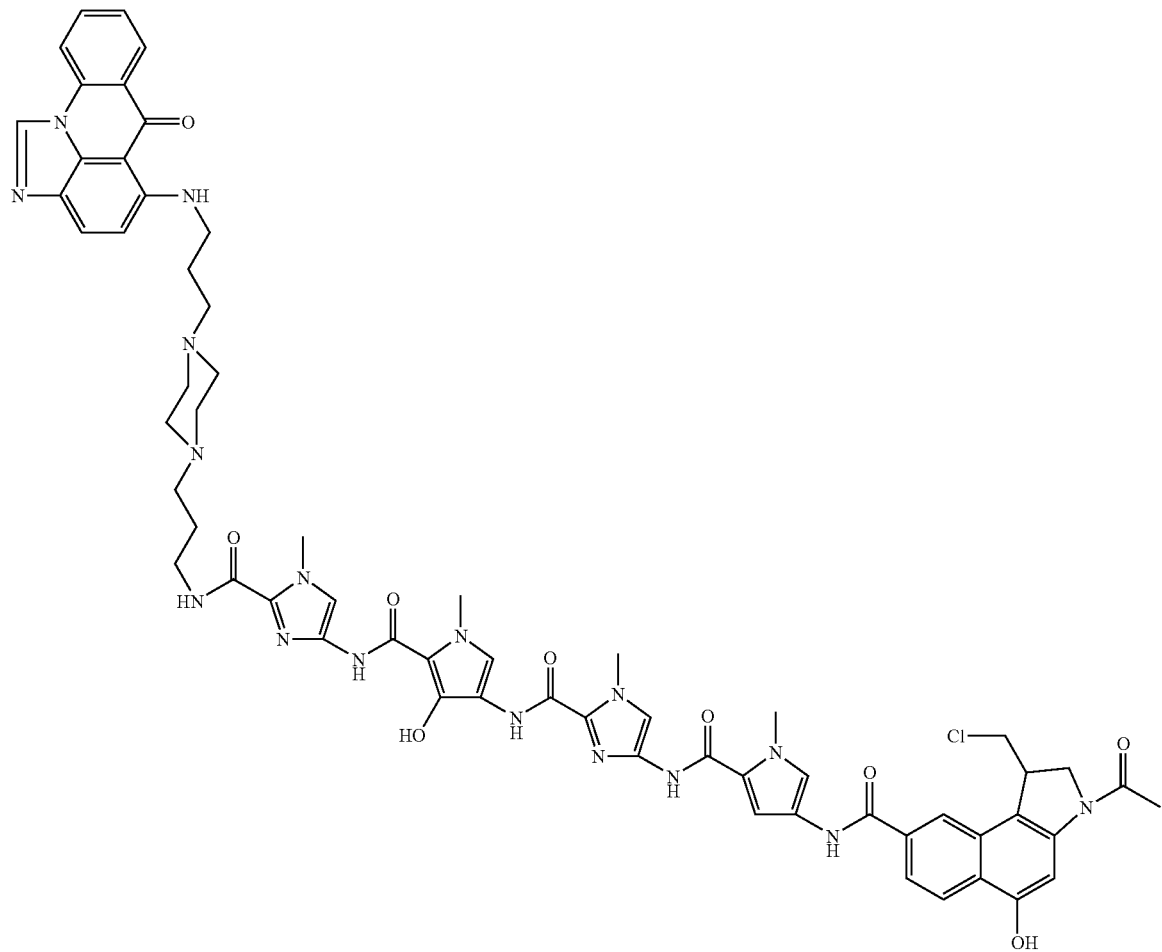

-continued

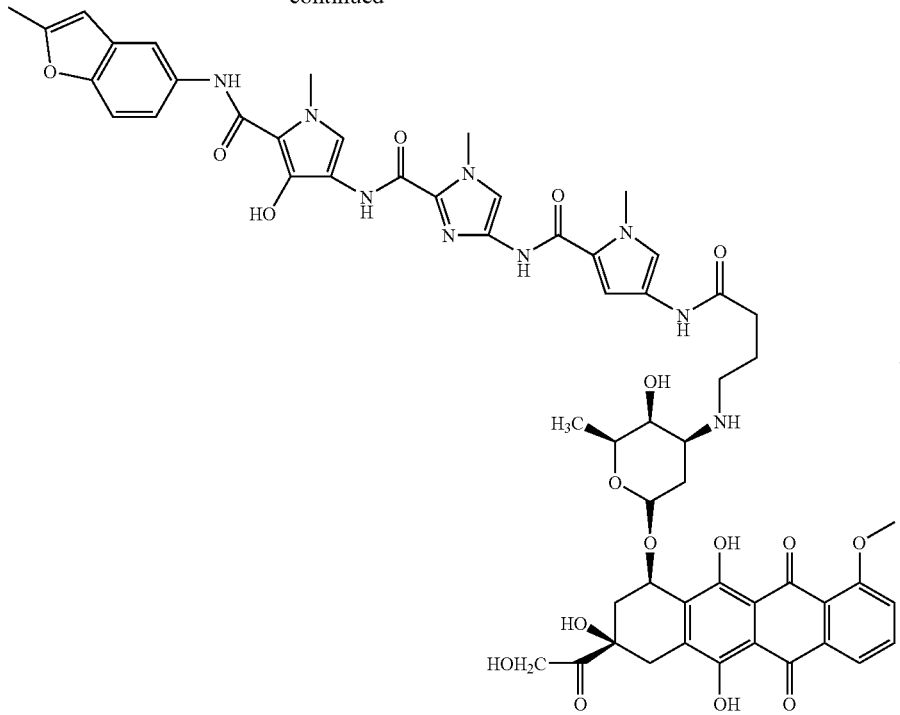

14. The conjugate of claim 11, wherein B is

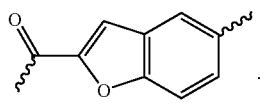

15. The conjugate of claim 11, wherein B is

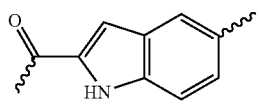

16. A conjugate of formula:

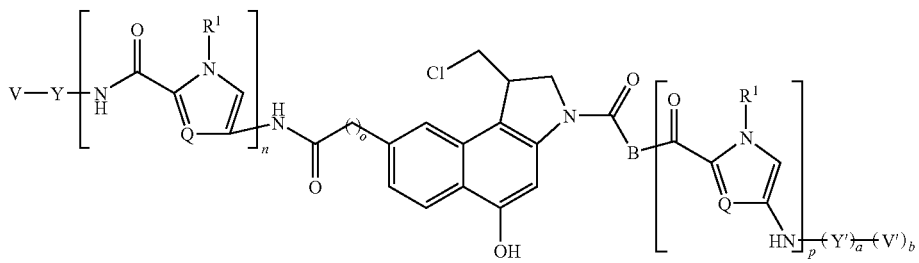

wherein
V and V' are the same or different and each is a substituted doxorubicin, a substituted daunorubicin, or a substituted imidazoacridone, wherein the substituent is selected from the group consisting of $C_{1-12}$ alkyl, $C_{3-8}$ cycloalkyl, $C_{6-30}$ aryl, $C_{5-30}$ heteroaryl, tolyl, xylyl, mesityl, anisyl, hydroxy, $C_{1-12}$ alkoxy, phenoxy, benzyloxy, acyloxy, halogen, cyano, benzyl, formyl, phenylcarbonyl, benzylcarbonyl, acetyl, carboxyl, carboxy-$C_{1-12}$ alkyl, carboxy-$C_{1-12}$ alkylamido, carboxy-$C_{1-12}$ dialkylamido, carboxamido, amino, $C_{1-12}$ alkylamino, $C_{1-12}$ dialkylamino, $C_{1-12}$ alkylcarbonyl, $C_{6-30}$ arylamino, $C_{6-30}$ diarylamino, mercapto, $C_{1-12}$ alkylthio, nitro, nitrophenyl, nitrobenzyl, $C_{1-12}$ trialkylsilyl, sulfonyl, $C_{1-12}$ trialkylammonium, pyrrolidinyl, dioxanyl, tetrahydrofuranyl, tetrahydropyranyl, piperidinyl, and morpholinyl, B is a heteroaromatic residue comprising subunits of 2-carbonyl- 1H-indole or 2-carbonyl-benzofuran, Y and Y' are the same or different and each is a bifunctional linker comprising a group selected from the group consisting of amino, $C_1$-$C_{12}$ alkylamino, $C_1$-$C_{12}$ dialkylamino, cycloalkylamino, piperazinyl, piperidinyl, pyrazinyl, purinyl, pyridazinyl, pyrrolidinyl, oxazolyl, isooxazolyl, quinolinyl, isoquinolinyl, byrimidinyl, morpholinyl, thiazolyl, isothiazolyl, quinoxalinyl, quinazolinyl, pyrrolyl, imidazolyl and an amino acid residue, in each repeat unit designated by n or p, Q is independently N or $CR^2$, $R^1$ and $R^2$ are the same or different and each is selected from the group consisting of hydrogen, $C_1$-$C_{12}$ alkyl, hydroxy, and halogen, n and p are independently 1 to 6, o is 0 or 1, and a and b are independently 0 to 1.

17. A pharmaceutical composition comprising the conjugate of claim 1, and a pharmaceutically acceptable carrier.

18. A pharmaceutical composition comprising the conjugate of claim 2 and a pharmaceutically acceptable carrier.

19. A pharmaceutical composition comprising the conjugate of claim 3 and a pharmaceutically acceptable carrier.

20. A pharmaceutical composition comprising the conjugate of claim 4 and a pharmaceutically acceptable carrier.

21. A pharmaceutical composition comprising the conjugate of claim 5 and a pharmaceutically acceptable carrier.

22. A pharmaceutical composition comprising the conjugate of claim 6 and a pharmaceutically acceptable carrier.

23. A pharmaceutical composition comprising the conjugate of claim 7 and a pharmaceutically acceptable carrier.

24. A pharmaceutical composition comprising the conjugate of claim 8 and a pharmaceutically acceptable carrier.

25. A pharmaceutical composition comprising the conjugate of claim 10 and a pharmaceutically acceptable carrier.

26. A pharmaceutical composition comprising the conjugate of claim 10 and a pharmaceutically acceptable carrier.

27. A pharmaceutical composition comprising the conjugate of claim 11 and a pharmaceutically acceptable carrier.

28. A pharmaceutical composition comprising the conjugate of claim 16 and a pharmaceutically acceptable carrier.

29. A method for treating cancer in a mammal comprising administering to a mammal in need thereof a cancer-treatment effective amount of the conjugate of claim 10, whereupon the mammal is treated for cancer.

30. A method for treating cancer in a mammal comprising administering to a mammal in need thereof a cancer-treatment effective amount of the conjugate of claim 1, whereupon the mammal is treated for cancer.

31. A method for treating cancer in a mammal comprising administering to a mammal in need thereof a cancer-treatment effective amount of the conjugate of claim 11, whereupon the mammal is treated for cancer.

32. A method for treating cancer in a mammal comprising administering to a mammal in need thereof a cancer-treatment effective amount of the conjugate of claim 16, whereupon the mammal is treated for cancer.

* * * * *

UNITED STATES PATENT AND TRADEMARK OFFICE
CERTIFICATE OF CORRECTION

PATENT NO. : 7,605,125 B2
APPLICATION NO. : 10/506085
DATED : October 20, 2009
INVENTOR(S) : Szekely et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1030 days.

Signed and Sealed this

Fifth Day of October, 2010

David J. Kappos
*Director of the United States Patent and Trademark Office*